United States Patent
Dong et al.

(10) Patent No.: US 10,647,673 B2
(45) Date of Patent: May 12, 2020

(54) ACETOPHENONE COMPOUND, PREPARATION METHOD THEREOF, AND APPLICATION THEREOF IN FATTY LIVER PREVENTION AND TREATMENT

(71) Applicant: Nanjing Bioenergy Medicine Science & Technology Co., Ltd., Nanjing (CN)

(72) Inventors: Yuqiong Dong, Shanghai (CN); Quanhai Liu, Shanghai (CN); Yu Shen, Shanghai (CN); Wentao Cai, Shanghai (CN)

(73) Assignee: Nanjing Bioenergy Medicine Science & Technology Co., Ltd., Nanjing (CN)

( * ) Notice: Subject to any disclaimer, the term of this patent is extended or adjusted under 35 U.S.C. 154(b) by 0 days.

(21) Appl. No.: 16/346,522

(22) PCT Filed: Mar. 15, 2018

(86) PCT No.: PCT/CN2018/079181
§ 371 (c)(1),
(2) Date: Apr. 30, 2019

(87) PCT Pub. No.: WO2018/166505
PCT Pub. Date: Sep. 20, 2018

(65) Prior Publication Data
US 2019/0292153 A1    Sep. 26, 2019

(30) Foreign Application Priority Data
Mar. 17, 2017    (CN) .......................... 2017 1 0161146

(51) Int. Cl.
| | |
|---|---|
| C07D 213/53 | (2006.01) |
| A61P 1/16 | (2006.01) |
| A61P 3/04 | (2006.01) |
| C07C 69/616 | (2006.01) |
| C07C 235/68 | (2006.01) |
| A61K 31/167 | (2006.01) |
| C07C 69/736 | (2006.01) |
| A61K 31/222 | (2006.01) |
| A61K 31/455 | (2006.01) |
| C07C 231/02 | (2006.01) |
| C07C 235/26 | (2006.01) |
| C07C 251/16 | (2006.01) |
| A61K 31/216 | (2006.01) |
| C07C 235/20 | (2006.01) |
| C07C 231/12 | (2006.01) |
| C07D 213/82 | (2006.01) |
| C07C 67/14 | (2006.01) |
| C07C 235/84 | (2006.01) |
| C07C 235/24 | (2006.01) |
| C07D 213/80 | (2006.01) |
| C07D 213/803 | (2006.01) |
| A61K 31/165 | (2006.01) |
| C07C 67/29 | (2006.01) |
| A61K 31/166 | (2006.01) |

(52) U.S. Cl.
CPC .......... *C07D 213/53* (2013.01); *A61K 31/165* (2013.01); *A61K 31/166* (2013.01); *A61K 31/167* (2013.01); *A61K 31/216* (2013.01); *A61K 31/222* (2013.01); *A61K 31/455* (2013.01); *A61P 1/16* (2018.01); *A61P 3/04* (2018.01); *C07C 67/14* (2013.01); *C07C 67/29* (2013.01); *C07C 69/616* (2013.01); *C07C 69/736* (2013.01); *C07C 231/02* (2013.01); *C07C 231/12* (2013.01); *C07C 235/20* (2013.01); *C07C 235/24* (2013.01); *C07C 235/26* (2013.01); *C07C 235/68* (2013.01); *C07C 235/84* (2013.01); *C07C 251/16* (2013.01); *C07D 213/80* (2013.01); *C07D 213/803* (2013.01); *C07D 213/82* (2013.01)

(58) Field of Classification Search
None
See application file for complete search history.

(56) References Cited

U.S. PATENT DOCUMENTS 2,393,820 A * 1/1946 Schnider .............. C07C 215/76
562/585

FOREIGN PATENT DOCUMENTS

| CN | 101108173 A | 1/2008 |
|---|---|---|
| CN | 102093246 A | 6/2011 |
| CN | 102838505 A | 12/2012 |

(Continued)

OTHER PUBLICATIONS

WIPO, State Intellectual Property Office of the P.R. China International Search Authority, International Search Report and Written Opinion dated Jun. 27, 2018 in International Patent Application No. PCT/CN2018/079181, 12 pages.

(Continued)

Primary Examiner — Zinna Northington Davis
(74) Attorney, Agent, or Firm — Inskeep IP Group, Inc.

(57) ABSTRACT

Disclosed is a compound represented by formula I or a pharmaceutically acceptable salt thereof, preparation method thereof, and use thereof in preventing or treating fatty liver or in preparing pharmaceuticals for weight loss.

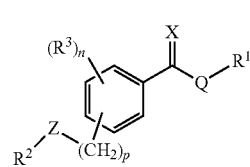

I

18 Claims, No Drawings

(56) References Cited

FOREIGN PATENT DOCUMENTS

| CN | 103087009 A | 5/2013 |
|---|---|---|
| CN | 104292120 A | 1/2015 |
| CN | 106146335 A | 11/2016 |

OTHER PUBLICATIONS

Munteanu, M.A. et al., "Current Management of NAFLD," *Clujul Medical* 2016 vol. 89 No. 1:19-23, 5 pages.

Milic, S. et al., "Nonalcoholic steatohepatitis: emerging targeted therapies to optimize treatment options," *Drug Design, Development and Therapy*, 2015:9 4835-4845, 11 pages.

Dehmel, F. et al., "Trithiocarbonates as a Novel Class of HDAC Inhibitors: SAR Studies, Isoenzyme Selectivity, and Pharmacological Profiles," *J. Med. Chem.*, 51(13), Jun. 18, 2008 (Jun. 18, 2008), ISSN:0022-2623, pp. 3985-4001, 17 pages.

"Database Registry[online]", STN International, Columbus, Ohio, USA., Aug. 11, 2006 (Aug. 11, 2006), CAS RN 900748-86-9, 1 page.

* cited by examiner

ACETOPHENONE COMPOUND, PREPARATION METHOD THEREOF, AND APPLICATION THEREOF IN FATTY LIVER PREVENTION AND TREATMENT

RELATED APPLICATIONS

This application is the United States National Stage entry under 35 U.S.C. 371 of PCT/CN2018/079181 entitled Acetophenone Compound, Preparation Method Thereof, And Application Thereof In Fatty Liver Prevention And Treatment filed on Mar. 15, 2018, which in turn claims the priority of Chinese patent application No. 201710161146.8 entitled Acetophenone Compound, Preparation Method Thereof, And Application Thereof In Fatty Liver Prevention And Treatment filed on Mar. 17, 2017, both of which are hereby incorporated by reference in their entireties.

FIELD OF THE INVENTION

The invention belongs to the field of design and synthesis of new medicaments, and particularly relates to novel aminoacetophenone-based compounds, preparation methods thereof, and uses thereof in preventing or treating fatty liver.

BACKGROUND OF THE INVENTION

Fat accounts for 3 to 5% of liver wet weight in a normal human liver. It would be called a fatty liver if more than ⅓ hepatocytes have steatosis histologically. The fat content may be up to 40 to 50% in some diseased livers. In general, fatty liver is actually relating to a group of diseases, for example from simple fatty liver (NAFLD) to steatohepatitis (NASH) and further developed to hepatic fibrosis wherein a considerable portion of people would eventually develop hepatic cirrhosis and a few people would eventually develop liver cancer. Thus, the development of medicaments for treating fatty liver has been highly valued.

In 1980, Jurge liudwig et al. reported hepatic steatosis in people who had low alcohol consumption per day. Over the next more than 30 years, researchers accumulated a large amount of evidences which can fully confirm this disease, such as the relationship between hepatic steatosis and obesity, and the clinical and biological differences including pathological morphological differences from alcoholic fatty liver. On this basis, the non-alcoholic fatty liver disease is identified as an independent disease. Further, researchers, especially in the past 10 years, have proven that steatohepatitis (NASH) is an independent and common disease that would develop severe diseases such as cirrhosis in a considerable number of people.

Due to lack of sensitive and specific diagnostic markers, the accuracy of epidemiological investigations of NAFLD is affected, and thus the epidemiological incidence of fatty liver is greatly underestimated. It is known that the sensitivity of ultrasound examination is higher than that of liver function test. In America, it was found that 20 to 30% of the population has over-standard triglyceride level in liver through measurement with magnetic resonance. Similar incidences were reported in recent years for Japan and China, while incidences vary from region to region in Africa with a general incidence of 10 to 20%. Thus, it is estimated that approximately 1 billion people have fatty liver worldwide. In recent years, fatty liver has risen from the third place to the first place among chronic liver diseases in incidence. According to statistics in America, the percentage of fatty liver among chronic liver diseases rose from 47% to 75% during the years 1988 to 2008. During this period, the five metabolic disease risk factors also had significant increase correspondingly, for example, the incidence of obesity rose from 24% to 33%, the incidence of visceral obesity rose from 35% to 51%, the incidence of type II diabetes rose from 5.6% to 9.1%, the incidence of insulin resistance rose from 2.3% to 3.5%, and the incidence of arterial hypertension rose from 22% to 34%. Meanwhile, fatty liver is closely related to these factors. The prevalence of obesity in patients with fatty liver is between 30 and 100%, and that of type II diabetes is between 10 and 75%. In Germany, the incidence of obesity in adults was 11.5% in 2000, and was 14.7% in 2010. In addition to the above factors, age and sex also play an important role. For example, the incidence of fatty liver is significantly higher in male older subjects and in subjects of Spanish ethnic origin. Therefore, many countries have issued clinical practice guidelines for non-alcoholic fatty disease/non-alcoholic fatty liver disease for NAFLD in recent years, and some research associations such as those in China, America, and Japan have issued their own guidelines.

In view of the high incidence and poor prognosis of fatty liver, various research institutions and pharmaceutical enterprises have begun to develop corresponding drugs. Since NAFLD is usually associated with metabolic disorders such as visceral obesity, IR, type II diabetes and dyslipidemia, the treatment would aim not only at liver disease, but also at these related metabolic disorders at the same time. However, the treatment could focus on the treatment of NAFLD if no related metabolic disease is accompanied by.

At present, effective methods for treating NAFLD/NASH include lifestyle interventions, surgical treatments, and drug treatments. The treatment of NAFLD depends on histopathological changes according to the treatment principle for NAFLD/NASH. If it is suggested through liver biopsy that a patient has only simple hepatic steatosis and no steatohepatitis or hepatic fibrosis, the patient would be recommended to change lifestyle, lose weight and increase physical activity. If a patient has severe obesity, surgery for treatment of obesity would be considered. For patients with NASH, the treatment depends on underlying diseases. If a patient has other underlying metabolic disorders such as IR (insulin resistance), type II diabetes, dyslipidemia, hypertension and obesity, these concomitant diseases need to be treated simultaneously.

For drug intervention, the drug treatment of NAFLD/NASH mainly directs to metabolic syndrome-related diseases, such as obesity, type II diabetes, dyslipidemia and hypertension. By now, there is no definitely effective drug for fatty liver, although many drugs have been used for evaluating the treatment of NAFLD/NASH. That is, the drugs that have been marketed have not been proven to be capable of treating fatty liver (Clujul Med. 2016, 89(1): 19-23; Drug Des Devel Ther, 2015, 20(9): 4835-4845). The development and research of drugs for treating fatty liver is booming currently.

During the exploration of drugs for treating fatty liver, there are mainly the following types of researches: 1. anti-fibrotic drugs used for treating NASH, such as Ceniciviroc, an inhibitor of C—C chemokine receptor types 2 and 5 (CCR2 and CCR5), which has been demonstrated to be capable of preventing and treating hepatic fibrosis and cirrhosis; 2. derivatives of bile acid, which usually are liver-related targets and have certain effect in treating non-alcoholic steatohepatitis according to the clinical data currently published, such as aramchol from Galmed Pharmaceuticals, which is a derivative obtained by combining fatty acid and bile acid; 3. galectin family, which can specifically recognize galactoside, such as GR-MD-02 which is a candidate inhibitor of galectin announced by Galectin Medical company to be capable of treating fatty liver and hepatic fibrosis; 4. peroxisome proliferator-activated receptor (PPAR), which is an important target for regulating sugar and lipid metabolism in vivo and improving insulin sensitivity, and good results have been achieved for screen of PPAR agonist compounds in the recent researches of fatty liver; 5. bile acid receptor FXR agonists, which are also in-depth researched for non-alcoholic fatty liver, and in which FXR is a member of the nuclear receptor family and involved in the metabolism of bilirubin. Preclinical studies showed that the activation of FXR can protect against liver damages induced by cholestasis. Obeticholic acid (OCA) is a derivative of chenodeoxycholic acid in natural bile of human, and has an agonistic effect on FXR 100 times more than chenodeoxycholic acid. It is shown by preliminary clinical trials that obeticholic acid is safe and effective. With further researches, obeticholic acid was approved by FDA as a drug for cholestatic cirrhosis (PBS) and had been marketed. However, obeticholic acid has serious side effect of itching, and the phase II clinical results obtained from fatty liver treatment in Japan are different from its expected effect. It was shown in Japan clinical trials that the effective dose of obeticholic acid was increased due to ethnic differences of patients, and the proportion of people with severe side effect of itching was as high as 70 to 90%. The clinical trials of fatty liver treatment are expected to finish in 2022 and final results could be known then.

In summary, obeticholic acid, a derivative of bile acid salt, has side effects of increasing blood lipids over a period of time and other side effects caused by bile acid salt, such as severe itching.

The present invention relates to novel aminoacetophenone-based compounds, and further derivatization and optimization thereof. Rats were fed with high fat diet to induce severe fatty liver, and administered with the optimized compounds to carry out efficacy researches. It was found from hepatic tissue pathological sections that hepatocyte steatosis, infiltration of mixed inflammatory cells in hepatic lobules, or cell infiltration with inflammation in the lobules severer than that in portal areas and fibrogenesis are significantly reduced as compared with those of the livers of rats in the model group. With comparison, it was demonstrated that the series of compounds of the present invention have clear and significant therapeutic effects on fatty liver, and also have significant hypolipidemic activity. By now, there is no report that similar compounds have related pharmacological effects. The present invention, for the first time, screened out a series of compounds having therapeutic effects for fatty liver through structural optimization and pharmacodynamic tests, thereby producing significant contributions to the field of treatment of fatty liver diseases.

Further, we found Compounds 13 and 14 of the present invention had obvious effects on weight loss by employing ob/ob obese diabetic mice and nutritive obesity C57 mice.

SUMMARY OF THE INVENTION

An object of the invention is to provide novel non-steroidal aminoacetophenone-based compounds which are obtained by linking an aminoacetophenone-based compound to a carboxylic compound with hypolipidemic effect through an amido bond. It is demonstrated by experiments that these compounds can reduce steatosis of hepatocytes in high-fat model animals and can treat fatty liver. Further, Compounds 13 and 14 have effects on weight loss.

In particular, the first aspect of the present invention provides a compound of Formula I:

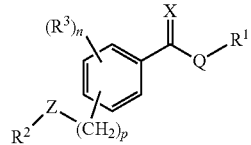

Formula I or a pharmaceutically acceptable salt thereof, wherein,
X is selected from oxygen, sulphur or —NH;
Z is selected from imino or oxygen;
Q is selected from a linear, branched or cyclic C1-C6 alkylene;
$R^1$ is selected from H, or

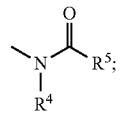

$R^2$ is selected from H, or

$R^3$ is independently selected from H; halogen; hydroxyl; amino; nitro; cyano; C1-C10 alkyl; C1-C10 alkoxyl; C3-C10 cycloalkyl; C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; substituted C1-C10 alkyl; substituted C3-C10 cycloalkyl; substituted formyl; substituted sulfonyl; substituted sulfone; or substituted sulfoxide,
n is an integer selected from 0 to 4;
p is an integer selected from 0 to 5;
wherein,
$R^4$ is selected from H or from substituted or unsubstituted C1-C10 alkyl, C3-C10 cycloalkyl;
$R^5$ or $R^6$ is independently selected from the optionally substituted groups of: phenyl; 5- to 6-membered monocyclic heteroaryl having 1 to 4 heteroatom(s) independently selected from nitrogen, oxygen or sulfur; or

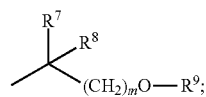

wherein $R^7$ or $R^8$ is independently selected from H or from substituted or unsubstituted C1-C10 alkyl, C3-C10 cycloalkyl;
$R^9$ is selected from phenyl, monosubstituted phenyl or multi-substituted phenyl, wherein the substituent for phenyl comprises halogen; hydroxyl; C1-C10 alkyl; C1-C10 alkoxyl; C3-C10 cycloalkyl; C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; substituted C1-C10 alkyl; substituted C3-C10 cycloalkyl; or, substituted formyl, m is an integer selected from 0 to 10;

said substituted includes substituents chosen from halogen; C1-C10 alkyl; C3-C10 cycloalkyl; C1-C10 alkyl substituted with C5-C10 aryl; C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; benzoyl; or, acylamino.

According to a preferred embodiment of the present invention, the compound of Formula I or a pharmaceutically acceptable salt thereof may be provided wherein:

X is selected from oxygen, sulphur or —NH;
Z is selected from imino or oxygen;
Q is selected from linear or branched C1-C3 alkyl;
$R^1$ is selected from H, or

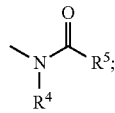

$R^2$ is selected from H, or

wherein $R^4$ is independently selected from H or from substituted or unsubstituted C1-C6 alkyl, C3-C6 cycloalkyl;

$R^3$ is independently selected from H; halogen; hydroxyl; amino; nitro; cyano; C1-C6 alkyl; C1-C6 alkoxyl; C3-C6 cycloalkyl; C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; substituted C1-C6 alkyl; substituted C3-C6 cycloalkyl; substituted formyl; substituted sulfonyl; substituted sulfone; or substituted sulfoxide, n is an integer selected from 0 to 4;
p is an integer selected from 0 to 5;
$R^5$ or $R^6$ is independently selected from the optionally substituted groups of: phenyl; 5- to 6-membered monocyclic heteroaryl having 1 to 4 heteroatom(s) independently selected from nitrogen, oxygen or sulfur; or,

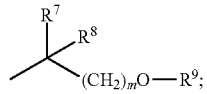

wherein $R^7$ or $R^8$ is independently selected from H or from substituted or unsubstituted C1-C6 alkyl, C3-C6 cycloalkyl;

$R^9$ is selected from phenyl, monosubstituted phenyl or multi-substituted phenyl, wherein the substituent for phenyl comprises halogen; hydroxyl; C1-C6 alkyl; C1-C6 alkoxyl; C3-C6 cycloalkyl; C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; substituted C1-C6 alkyl; substituted C3-C6 cycloalkyl; or, substituted formyl, m is an integer selected from 0 to 8.

According to a more preferred embodiment of the present invention, the compound of Formula I or a pharmaceutically acceptable salt thereof may be provided wherein:

X is oxygen;
Z is selected from imino or oxygen;
Q is methyl or methylene;
$R^1$ is selected from H, or

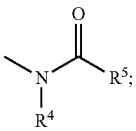

$R^2$ is selected from H, or

wherein $R^4$ is independently selected from H or from substituted or unsubstituted C1-C10 alkyl, C3-C10 cycloalkyl;

$R^3$ is independently selected from H; halogen; hydroxyl; amino; nitro; cyano; C1-C6 alkyl; C1-C6 alkoxyl; C3-C6 cycloalkyl; C1-C6 alkyl having a C5-C10 aryl ring, C5-C10 aryl; 3- to 10-membered heterocyclic group having 1 to 3 heteroatom(s) independently selected from nitrogen, oxygen or sulfur; 5- to 10-membered heteroaryl having 1 to 4 heteroatom(s) independently selected from nitrogen, oxygen or sulfur; substituted C1-C6 alkyl; substituted C3-C6 cycloalkyl; substituted formyl; substituted sulfonyl; substituted sulfone; or substituted sulfoxide, n is an integer selected from 0 to 1;
p is an integer selected from 0 to 5
$R^5$ or $R^6$ is independently selected from the optionally substituted groups of: phenyl; 5- to 6-membered monocyclic heteroaryl having 1 to 4 heteroatom(s) independently selected from nitrogen or oxygen; or,

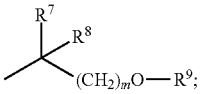

$R^7$ or $R^8$ is independently selected from H or from substituted or unsubstituted C1-C6 alkyl;

$R^9$ is independently selected from monosubstituted phenyl or disubstituted phenyl, wherein the substituent for phenyl is halogen, C1-C6 alkyl or C1-C6 alkoxyl;

m is an integer selected from 0 to 5.

According to a particularly preferred embodiment of the present invention, $R^5$ and $R^6$ are pyridin-3-yl.

According to a particularly preferred embodiment of the present invention, $R^7$ and $R^8$ are methyl.

According to a particularly preferred embodiment of the present invention, $R^9$ is 2,5-dimethyl phenyl.

According to a particularly preferred embodiment of the present invention, m is 3.

According to a particularly preferred embodiment of the present invention, the halogen is chlorine; $R^4$ is H.

According to a particularly preferred embodiment of the present invention, the compound of Formula I of the present invention may be any of the following compounds:

01

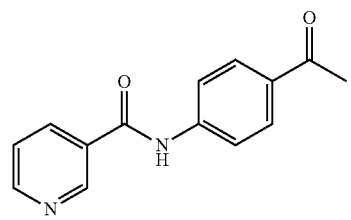
,

02

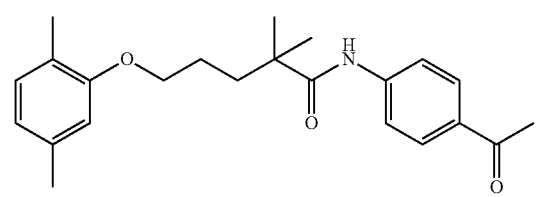
,

03

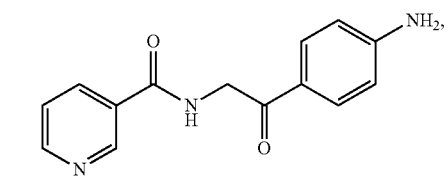
,

04

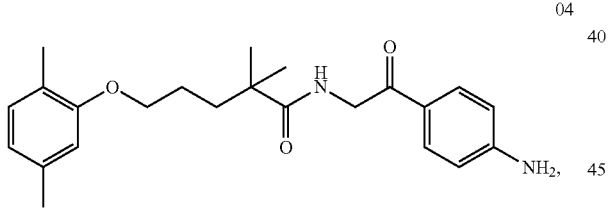
,

05

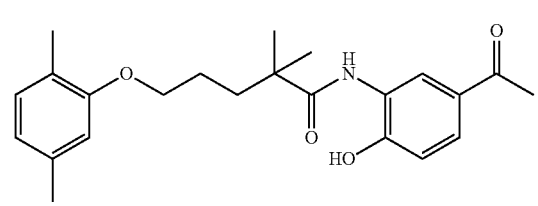
,

06

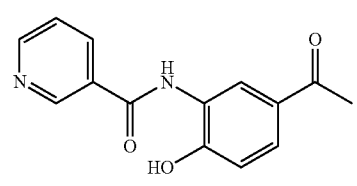
,

07

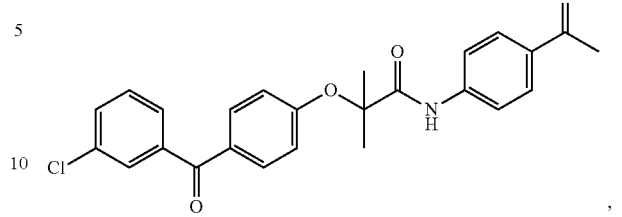
,

08

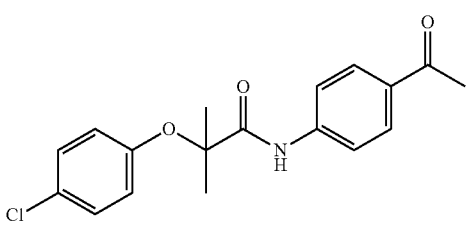
,

09

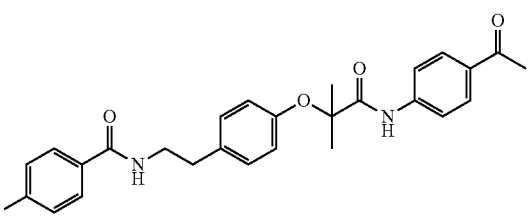
,

10

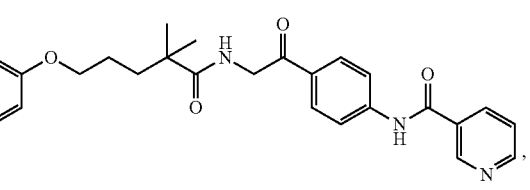
,

11

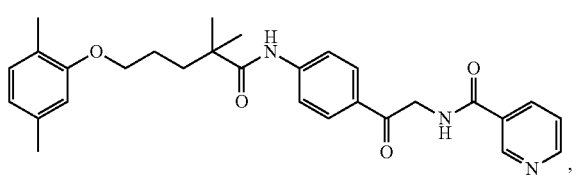
,

12

-continued

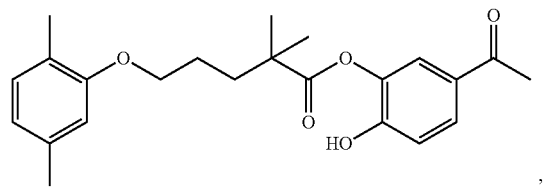
, 13

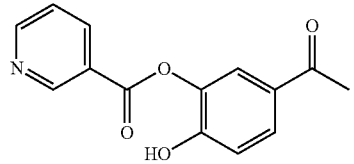
, 14

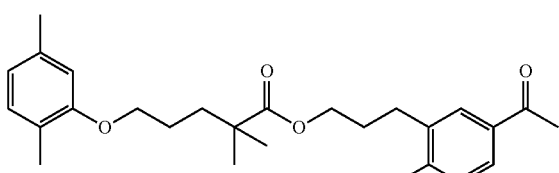
, 15

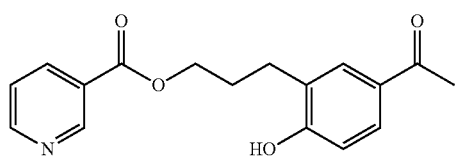
, 16

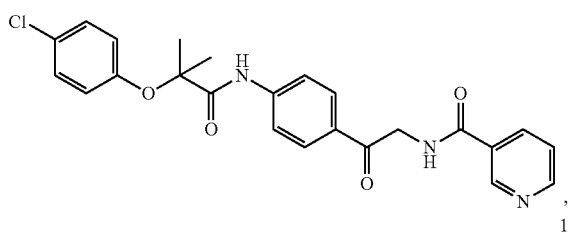
, 17

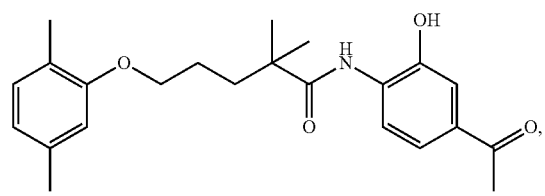
, 18

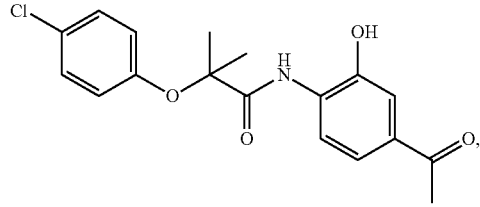
, 19

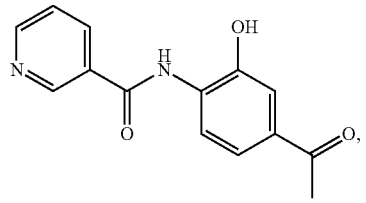
, 20

-continued

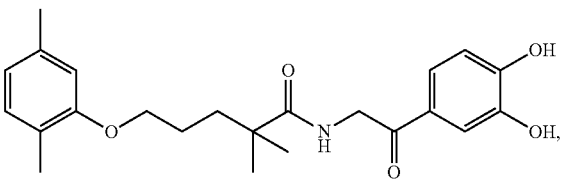
, 21

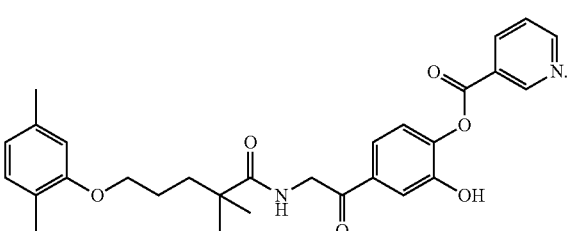
, 22

Unless otherwise stated, the following terms in this specification and claims of the present invention have the following meanings.

The term "alkyl" as used herein is intended to comprise a branched or linear saturated aliphatic hydrocarbon group having specified number of carbon atoms. For example, C1-C10 in "C1-C10 alkyl" is defined to comprise a saturated aliphatic hydrocarbon group having 1, 2, 3, 4, 5, 6, 7, 8, 9 or 10 carbon atoms in a linear or branched structure. The term "C1-C10 alkyl" specifically comprises methyl, ethyl, n-propyl, isopropyl, n-butyl, t-butyl, isobutyl, pentyl, hexyl, heptyl, octyl, nonyl, decyl and the like.

The term "alkylene" refers to a divalent saturated hydrocarbon group. For example, methylene refers to —CH$_2$—, ethylene refers to —CH$_2$CH$_2$— or —CH(CH$_3$)—, and the like.

The term "alkoxyl" refers to a branched or linear saturated aliphatic hydrocarbon group having specified number of carbon atoms, which is linked though an oxygen bridge.

The term "cycloalkyl" refers to a saturated or partially unsaturated monocyclic, polycyclic or bridge-linked carbocyclic substituent. For example, a cyclic group having 3 to 20 carbon atoms can be represented by C3-20 cycloalkyl; a cyclic group having 5 to 15 carbon atoms can be represented by a C5-15 cycloalkyl; a cyclic group having 3 to 8 carbon atoms can be represented by C3-8 cycloalkyl, and the like. This term may comprise, but is not limited to, cyclopropyl, cyclobutyl, cyclopentyl, cyclohexyl, cycloheptyl, cyclooctyl, 1H-indenyl, 2,3-dihydro-indenyl, 1,2,3,4-tetrahydronaphthyl, 5,6,7,8-tetrahydro-naphthyl, 8,9-dihydro-7H-benzocycloheptene-6-yl, 6,7,8,9-tetrahydro-5H-benzocycloheptenyl, 5,6,7,8,9,10-hexahydro-benzocyclooctenyl, fluorenyl, bicyclo[2.2.1]heptyl, bicyclo[2.2.1]heptenyl, bicyclo[2.2.2]octyl, bicyclo[3.1.1]heptyl, bicyclo[3.2.1 l]octyl, bicyclo[2.2.2]octenyl, bicyclo[3.2.1 l]octenyl, adamantyl, octahydro-4,7-methylene-1H-indenyl, octahydro-2,5-methylene-cyclopentadienyl and the like. The substituent of cycloalkyl may be attached to a central molecule via any suitable carbon atom(s) and may be further substituted when permitted.

The term "aryl" as used herein refers to any stable monocyclic or bicyclic carbocyclic group which may contain up to 7 atoms in each ring, wherein at least one ring is an aromatic ring. Examples of the above aryl unit may comprise phenyl, naphthyl, tetrahydronaphthyl, 2,3-dihydro-indenyl, biphenyl, phenanthryl, anthryl or acenaphthyl. It would be understood that, if an aryl substituent is a bicyclic substituent and one of the rings is a non-aromatic ring, the linking is achieved through the aromatic ring.

The term "heteroaryl" as used herein indicates a stable monocyclic or bicyclic group having up to 7 atoms in each ring, wherein at least one ring is an aromatic ring and the "heteroaryl" has 1 to 4 heteroatom(s) selected from O, N, and S. Within the scope of this definition, heteroaryl comprises, but is not limited to, acridinyl, carbazolyl, cinnolinyl, quinoxalinyl, pyrazolyl, indolyl, benzotriazolyl, furyl, thienyl, benzothienyl, benzofuranyl, quinolyl, isoquinolyl, oxazolyl, isoxazolyl, indolyl, pyrazinyl, pyridazinyl, pyridyl, pyrimidinyl, pyrrolyl, tetrahydroquinolyl. As defined below for heterocycle, "heteroaryl" should be further understood to include any N-oxide derivative of nitrogen-containing heteroaryl. If a heteroaryl substituent is a bicyclic substituent in which one ring is a non-aromatic ring or does not contain any heteroatom, it should be understood that the linking is done by an aromatic ring or by a heterocyclic ring, respectively.

The term "heterocycle" or "heterocyclyl" as used herein indicates a 5- to 10-membered non-aromatic heterocyclic group containing 1 to 4 heteroatom(s) selected from O, N and S, and may comprise a bicyclic group. Thus, "heterocyclyl" comprises the above heteroaryl and dihydro- or tetrahydro-analogues thereof. Other examples of "heterocyclyl" comprise, but are not limited to, benzimidazolyl, benzofuranyl, benzofuroxan, benzopyrazolyl, benzotriazolyl, benzothienyl, benzoxazolyl, carbazolyl, carbolinyl, cinnolinyl, furyl, imidazolyl, indolinyl, indolyl, indazolyl, isobenzofuranyl, isoindolyl, isoquinolyl, isothiazolyl, isoxazolyl, naphthylpyrimidinyl, oxadiazolyl, oxazolyl, oxazolinyl, isooxazolinyl, oxocyclobutyl, pyranyl, pyrazinyl, pyrazolyl, pyridazinyl, pyridopyridinyl, pyridazinyl, pyridyl, pyrimidinyl, pyrrolyl, quinazolinyl, quinolyl, quinoxalinyl, tetrahydropyranyl, tetrazolyl, tetrazolylpyridyl, thiadiazolyl, thiazolyl, thienyl, triazolyl, azetidinyl, 1,4-dioxanyl, hexahydroazapinyl, piperazinyl, piperidinyl, pyrrolidinyl, morpholinyl, thiomorpholinyl, dihydrobenzimidazolyl, dihydrobenzofuranyl, dihydrob enzothiophenyl, dihydrobenzoxazolyl, dihydrofuranyl, dihydroimidazolyl, dihydroindolyl, dihydroisoxazolyl, dihydroisothiazolyl, dihydrooxadiazolyl, dihydrooxazolyl, dihydropyrazinyl, dihydropyrazolyl, dihydropyridyl, dihydropyrimidinyl, dihydropyrrolyl, dihydroquinolyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl and tetrahydrothienyl, as well as N-oxides thereof. A heterocyclic substituent may be linked via a carbon- or hetero-atom.

In the present invention, the pharmaceutically acceptable salt is preferably an acid addition salt obtained by a reaction of a compound of the present invention with a pharmaceutically acceptable acid, or a salt obtained by a reaction of a compound having an acidic group with a basic compound. Said acid is preferably selected from inorganic acids such as hydrochloric acid, sulfuric acid, phosphoric acid or hydrobromic acid, or from organic acids such as oxalic acid, maleic acid, fumaric acid, malic acid, tartaric acid, citric acid or benzoic acid. Said basic compound is preferably selected from sodium hydroxide, potassium hydroxide, calcium hydroxide, sodium carbonate, potassium bicarbonate or the like. The above pharmaceutically acceptable salt may be easily isolated, and can be purified by conventional isolation methods such as solvent extraction, dilution, recrystallization, column chromatography, and preparative thin layer chromatography.

The second aspect of the present invention provides a method for preparing the above compound of Formula I or a pharmaceutically acceptable salt thereof.

In general, the compound of Formula I in which $R^2$ is

which may be represented by Formula I-A, can be prepared by the following Process 1.

Process 1

Process 1 provides two methods for preparing the compound represented by Formula I-A.

Method I may comprise a step of directly condensing an acid with a compound in the presence of a condensing agent and a solvent.

According to a preferred embodiment of the present invention, the condensing agent is a commonly used condensing agent for amide such as 2-(7-azobenzotriazole)-N,N,N',N'-tetramethyluronium hexafluorophosphate, N,N'-carbonyldiimidazole, dicyclohexylcarbodiimide, diisopropylcarbodiimide, and the like.

According to a preferred embodiment of the present invention, the solvent is selected from amide-based solvents such as N,N-dimethylformamide, N,N'-dimethylacetamide and N-methylpyrrolidone; halohydrocarbon such as dichloromethane, dichloroethane and chloroform; ester solvents such as ethyl acetate and isopropyl acetate; or cyclic ether solvents such as tetrahydrofuran and dioxane.

According to a preferred embodiment of the present invention, a nitrogen-containing catalyst such as N,N-dimethylaminopyridine may be added to accelerate the reaction.

Method II may comprise steps of: 1) reacting an acid

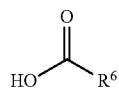

with a chlorinating agent to give corresponding acyl chloride; and 2) condensing the acyl chloride and the compound

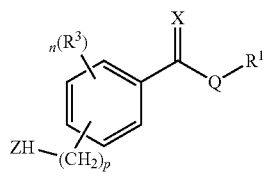

in a solvent.

According to a preferred embodiment of the present invention, the chlorinating agent comprises oxalyl chloride, thionyl chloride, phosphorus trichloride, phosphorus pentachloride, and the like.

According to a preferred embodiment of the present invention, the solvent is selected from amide-based solvents such as N,N-dimethylformamide, N,N'-dimethylacetamide and N-methylpyrrolidone; halohydrocarbon such as dichloromethane, dichloroethane and chloroform; ester solvents such as ethyl acetate and isopropyl acetate; or cyclic ether solvents such as tetrahydrofuran and dioxane.

According to a preferred embodiment of the present invention, the condensation reaction can be accelerated by adding an inorganic base such as sodium hydroxide, potassium hydroxide, sodium carbonate and potassium carbonate, or an organic base such as triethylamine, pyridine and diisopropylethylamine.

In general, the compound of Formula I, in which Z is imino, $R^2$ is H, and $R^1$ is acylamino, is represented by Formula I-B and can be prepared by Process 2 as follows:

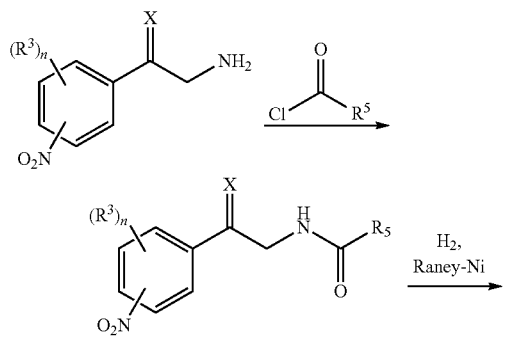

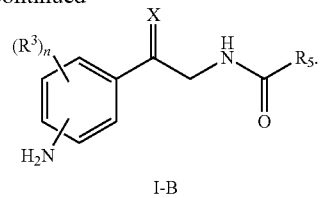

I-B

In Process 2, a first step comprises reacting an acid

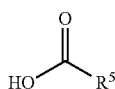

with a chlorinating agent to give corresponding acyl chloride; and condensing the acyl chloride and an amine compound

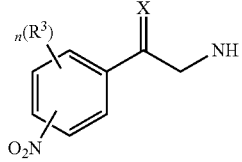

in a solvent.

According to a preferred embodiment of the present invention, the chlorinating agent comprises oxalyl chloride, thionyl chloride, phosphorus trichloride, phosphorus pentachloride, and the like.

According to a preferred embodiment of the present invention, the solvent is selected from amide-based solvents such as N,N-dimethylformamide, N,N'-dimethylacetamide and N-methylpyrrolidone; halohydrocarbon such as dichloromethane, dichloroethane and chloroform; ester solvents such as ethyl acetate and isopropyl acetate; or cyclic ether solvents such as tetrahydrofuran and dioxane.

According to a preferred embodiment of the present invention, the condensation reaction can be accelerated by adding an inorganic base such as sodium hydroxide, potassium hydroxide, sodium carbonate and potassium carbonate, or an organic base such as triethylamine, pyridine and diisopropylethylamine.

In a second step, the nitro-containing compound is reduced through hydrogenation in the presence of a hydrogenation catalyst and a solvent, or is reduced to amino in the presence of a reducing agent and a solvent.

According to a preferred embodiment of the present invention, the hydrogenation catalyst may comprise Raney nickel, palladium carbon, platinum carbon and the like.

According to a preferred embodiment of the present invention, the solvent may be selected from water; alcohol solvents such as methanol, ethanol and isopropanol; halogenated hydrocarbons such as dichloromethane, dichloroethane and chloroform; ester solvents such as ethyl acetate and isopropyl acetate; or cyclic ether solvents such as tetrahydrofuran and dioxane.

According to a preferred embodiment of the present invention, the reducing agent may comprise iron powder/ammonium chloride, stannous chloride, sodium dithionite, sodium sulfide, and the like.

The third aspect of the present invention provides a class of pharmaceutical compositions, comprising the compound of Formula I or a pharmaceutically acceptable salt thereof, as well as a pharmaceutically acceptable additive.

The compounds of the present invention can be formulated into pharmaceutical compositions with various pharmaceutically conventional additives such as diluents and excipients. Depending on therapeutic purposes, the pharmaceutical compositions can be formulated into various types of unit dosage forms for administration, such as tablet, pill, powder, solution, suspension, emulsion, granule, capsule, suppository and injection (solution or suspension).

Any excipient known and widely used in the art can be used in order to form the pharmaceutical compositions into tablets. For example, the excipient can be a carrier such as lactose, white sugar, sodium chloride, glucose, urea, starch, calcium carbonate, kaolin, crystalline cellulose, and silicic acid; a binder such as water, ethanol, propanol, common syrup, glucose solution, starch solution, gelatin solution, carboxymethyl cellulose, shellac, methyl cellulose, potassium phosphate, and polyvinylpyrrolidone; a disintegrating agent such as dry starch, sodium alginate, agar powder and kelp powder, sodium bicarbonate, calcium carbonate, fatty acid ester of polyethylene sorbitol, sodium lauryl sulfate, monoglyceride stearate, starch and lactose; a disintegration inhibitor such as white sugar, glyceryl tristearate, coconut oil and hydrogenated oil; an adsorption enhancer such as quaternary ammonium bases and sodium lauryl sulfate; a wetting agent such as glycerin and starch; an adsorbent such as starch, lactose, kaolin, bentonite and colloidal silicic acid; or a lubricant such as pure talc, stearate, boric acid powder and polyethylene glycol. If desired, the tablet might be a sugar-coated tablet, an enteric-coated tablet, a film-coated tablet (e.g. a gelatin film-coated tablet), a two-layer film-coated tablet or a multilayer-coated tablet by using conventional coating materials.

Any excipient known and widely used in the art may be used in order to form the pharmaceutical composition into pills. For example, the excipient can be a carrier such as lactose, starch, coconut oil, hardened vegetable oil, kaolin and talc; a binder such as acacia gum powder, tragacanth gum powder, gelatin and ethanol; or a disintegrating agent such as agar and kelp powder.

Any excipient known and widely used in the art may be used in order to form the pharmaceutical composition into suppository. For example, the excipient can be polyethylene glycol, coconut oil, higher alcohols, esters of higher alcohols, gelatin, semi-synthetic glycerides, and the like.

In order to prepare a pharmaceutical composition in an injection form, the solution or suspension may be sterilized and preferably added with an appropriate amount of sodium chloride, glucose, glycerin or the like so as to prepare an injection which is isotonic with blood. Any carrier commonly used in the art can be used for preparing the injection. For example, the carrier may be water, ethanol, propylene glycol, ethoxylated isostearyl alcohol, polyoxylated isostearyl alcohol, fatty acid ester of polyethylene sorbitol and the like. In addition, a conventional dissolving agent, buffer, analgesic or the like can be further added.

The content of the compound shown by Formula I of the invention or a pharmaceutically acceptable salt thereof in the pharmaceutical composition is not specially limited, and can be selected within a wide range. It generally can be 1 to 70% by weight, preferably 1 to 30% by weight.

There is no special limitation to the administration route of the pharmaceutical composition in the present invention. A formulation of a suitable dosage form can be selected for administration depending on the age, sex and other conditions and symptoms of the patient.

For example, the pharmaceutical composition in a tablet, pill, solution, suspension, emulsion, granule or capsule form can be administered orally; the pharmaceutical composition in an injection form can be administered alone or be administered intravenously in combination with injectable solution such as glucose solution or amino acid solution, and if necessary, the injection can be used alone for intramuscular, intradermal, subcutaneous or intraperitoneal injection; and the pharmaceutical composition in a suppository form can be administered into rectum.

In the present invention, the administration dose can be appropriately selected depending on the administration method, the age, sex, and other conditions and symptoms of the patient. A typical administration dose may be about 0.1 to 300 mg pharmaceutically active ingredient/kg body weight/day. Generally, each unit dosage form may comprise 1 to 200 mg of the pharmaceutically active ingredient.

The fourth aspect of the present invention provides the use of the compound of Formula I or a pharmaceutically acceptable salt thereof in the manufacture of a medicament for preventing or treating fatty liver or for losing weight.

The present invention comprises the following beneficial effects. The compounds of the present invention have good prevention and/or treatment effect for mouse pathological models of fatty liver. It is especially important that the compounds provided herein are less toxic. Further, it has been found that compounds of this type not only reduce the level of triglyceride in blood of high-fat model animals, but also have good effects in lowering cholesterol and low-density lipoprotein.

DETAILED DESCRIPTION OF THE EMBODIMENTS

Example 1: Preparation of Compound 01

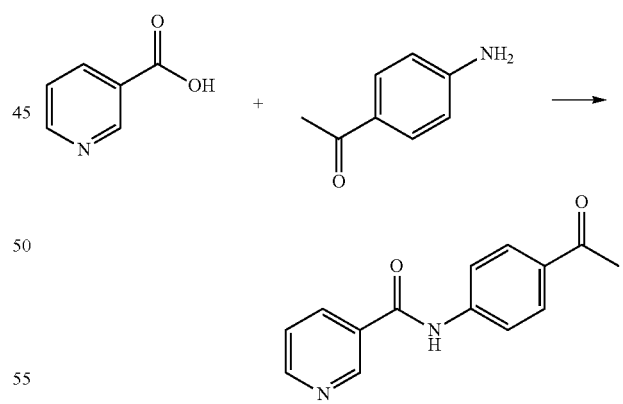

3.0 g of p-aminoacetophenone and 2.5 g of nicotinic acid were dissolved in 20 mL of N,N-dimethylformamide, and 11.4 g of 2-(7-azobenzotriazole)-N,N,N',N'-tetramethyluronium hexafluorophosphate and 7.8 g of diisopropylethylamine were added. The resulted mixture was stirred at room temperature for 2 hours, washed by adding 150 mL of ethyl acetate, and then washed successively with 30 mL of water and 30 mL of saturated brine. Then, the solvent was evaporated to dryness, and 2.5 g of the target compound was obtained through silica-gel column chromatography. $^1$H NMR (400 MHz, DMSO-d$_6$) δ 10.69 (d, J=19.2 Hz, 1H), 9.09 (t, J=9.7 Hz, 1H), 8.79-8.70 (m, 1H), 8.32-8.23 (m, 1H), 7.97 (d, J=8.8 Hz, 2H), 7.91 (d, J=8.8 Hz, 2H), 7.59-7.50 (m, 1H), 2.54 (s, 3H). MS (ESI) m/z: 241.0 [M+1]$^+$.

Example 2: Preparation of Compound 02

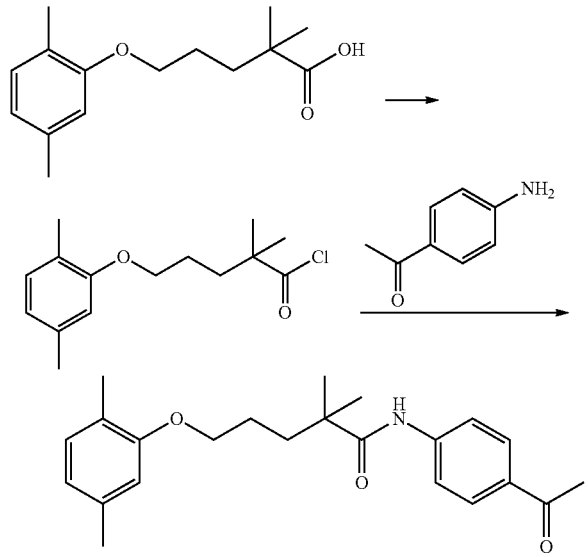

4.0 g of 5-(2,5-dimethylphenoxy)-2,2-dimethylpentanoic acid was dissolved in 40 mL of dichloromethane, and 3.0 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

2.2 g of p-aminoacetophenone was dissolved in 30 mL of pyridine, and the above acyl chloride in 20 mL of dichloromethane solution was added dropwise under cooling in an ice bath. After addition, the ice bath was removed; the mixture was warmed to room temperature and stirred for 1 hour. The solvent was evaporated to dryness, and the residue was dissolved by adding 200 mL of ethyl acetate, and washed successively with 100 mL of 3N hydrochloric acid, 100 mL of water and 100 mL of saturated brine. Then, the solvent was evaporated to dryness, and 5.4 g of the target compound was obtained through silica-gel column chromatography. $^1$H NMR (400 MHz, CDCl$_3$) δ 7.95-7.89 (m, 2H), 7.62 (d, J=8.8 Hz, 2H), 7.56 (s, 1H), 6.99 (d, J=7.5 Hz, 1H), 6.66 (d, J=7.5 Hz, 1H), 6.59 (s, 1H), 3.97-3.88 (m, 2H), 2.57 (s, 3H), 2.28 (s, 3H), 2.14 (s, 3H), 1.82 (dd, J=15.4, 2.8 Hz, 4H), 1.35 (s, 6H). MS (ESI) m/z: 390.2 [M+23]$^+$.

Example 3: Preparation of Compound 03

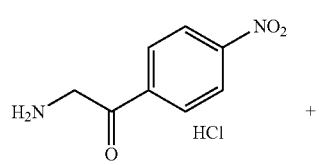

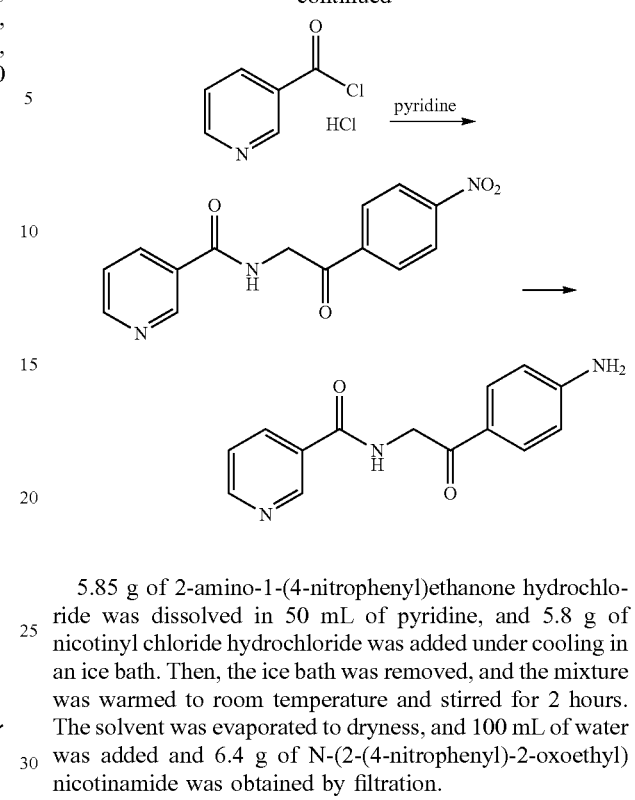

5.85 g of 2-amino-1-(4-nitrophenyl)ethanone hydrochloride was dissolved in 50 mL of pyridine, and 5.8 g of nicotinyl chloride hydrochloride was added under cooling in an ice bath. Then, the ice bath was removed, and the mixture was warmed to room temperature and stirred for 2 hours. The solvent was evaporated to dryness, and 100 mL of water was added and 6.4 g of N-(2-(4-nitrophenyl)-2-oxoethyl)nicotinamide was obtained by filtration.

The above N-(2-(4-nitrophenyl)-2-oxoethyl)nicotinamide was dissolved in a mixed solvent of 50 mL of dichloromethane and 100 mL of methanol, and added with 2.0 g of Raney nickel. The resulted mixture was stirred overnight at room temperature in a hydrogen atmosphere. The catalyst was removed by filtration, and the solvent of the filtrate was evaporated to dryness. 1.4 g of the target compound was obtained through silica-gel column chromatography. $^1$H NMR (400 MHz, DMSO-d$_6$) δ 9.04 (d, J=1.7 Hz, 1H), 8.90 (t, J=5.6 Hz, 1H), 8.71 (dd, J=4.8, 1.5 Hz, 1H), 8.21 (m, 1H), 7.72 (m, 2H), 7.51 (m, 1H), 6.57 (t, J=9.5 Hz, 2H), 6.11 (s, 2H), 4.68-4.59 (m, 2H). MS (ESI) m/z: 256.0 [M+1]$^+$.

Example 4: Preparation of Compound 04

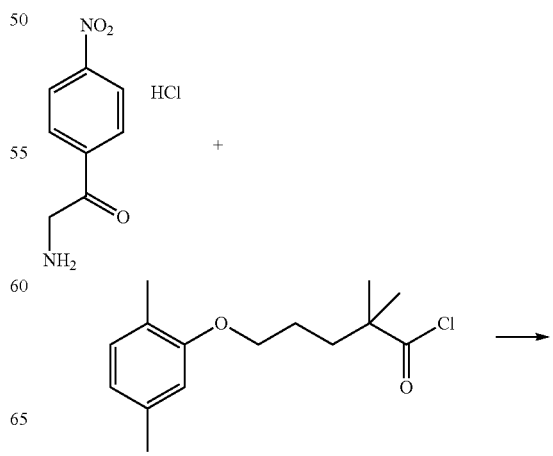

-continued

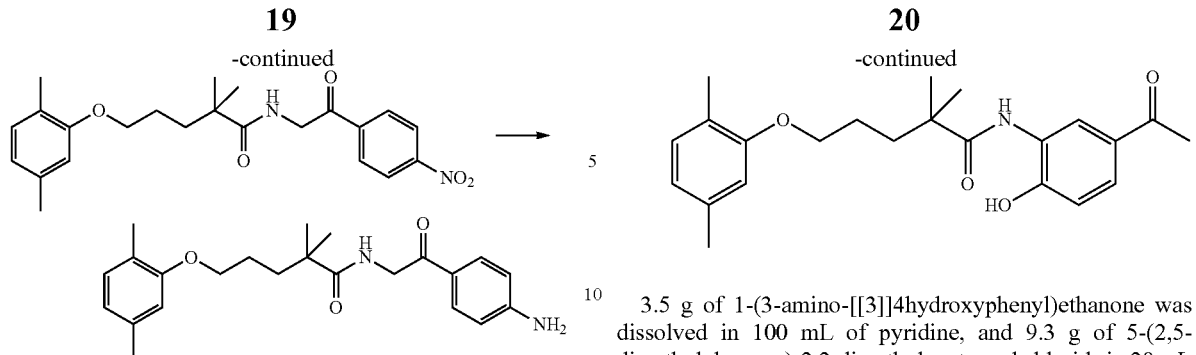

8.0 g of 5-(2,5-dimethylphenoxy)-2,2-dimethylpentanoic acid was dissolved in 100 mL of dichloromethane, and 6.1 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

6.9 g of 2-amino-1-(4-nitrophenyl)ethanone hydrochloride was dissolved in 80 mL of pyridine, and the above acyl chloride in 50 mL of dichloromethane solution was added dropwise under cooling in an ice bath. After addition, the ice bath was removed; the mixture was warmed to room temperature and stirred for 2 hours. The solvent was evaporated to dryness, and the residue was dissolved by adding 200 mL of ethyl acetate, and washed successively with 100 mL of 3N hydrochloric acid, 100 mL of water and 50 mL of saturated brine. The solvent was evaporated to dryness, and 6.2 g of 5-(2,5-dimethylphenoxy)-2,2-dimethyl-N-(2-(4-nitrophenyl)-2-oxoethyl)-pentanamide was obtained through silica-gel column chromatography.

The above 5-(2,5-dimethylphenoxy)-2,2-dimethyl-N-(2-(4-nitrophenyl)-2-oxoethyl)pentan-amide was dissolved in 100 mL of methanol, 1.0 g of Raney nickel was added, and the mixture was stirred overnight at room temperature in a hydrogen balloon atmosphere. The catalyst was removed by filtration, and the solvent of the filtrate was evaporated to dryness. 3.5 g of the target compound was obtained through silica-gel column chromatography. $^1$H NMR (400 MHz, CDCl$_3$) δ 7.80 (d, J=8.7 Hz, 2H), 6.98 (d, J=7.4 Hz, 1H), 6.89 (s, 1H), 6.63 (m, 4H), 4.62 (d, J=4.0 Hz, 2H), 4.27 (s, 2H), 3.91 (d, J=4.8 Hz, 2H), 2.29 (s, 3H), 2.16 (s, 3H), 1.80-1.72 (m, 4H), 1.29 (s, 6H). MS (ESI) m/z: 384 [M+1]$^+$.

Example 5: Preparation of Compound 05

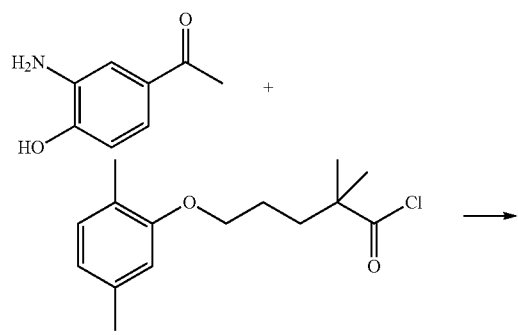

3.5 g of 1-(3-amino-[[3]]4hydroxyphenyl)ethanone was dissolved in 100 mL of pyridine, and 9.3 g of 5-(2,5-dimethylphenoxy)-2,2-dimethylpentanoyl chloride in 20 mL of dichloromethane solution was added dropwise under cooling in an ice bath. After addition, the ice bath was removed, and the mixture was warmed to room temperature and stirred for 2 hours. The solvent was evaporated to dryness, and the residue was dissolved by adding 200 mL of ethyl acetate, and washed successively with 100 mL 3N hydrochloric acid, 60 mL of water and 30 mL of saturated brine. Then, the solvent was evaporated to dryness, and 5.1 g of the target compound was obtained through recrystallization using ethyl acetate as the solvent. $^1$H NMR (400 MHz, CDCl$_3$) δ 9.99 (s, 1H), 7.82 (s, 1H), 7.71 (dt, J=6.2, 2.0 Hz, 2H), 7.04 (d, J=8.3 Hz, 1H), 6.99 (d, J=7.4 Hz, 1H), 6.65 (d, J=7.5 Hz, 1H), 6.60 (s, 1H), 3.95 (t, J=5.4 Hz, 2H), 2.53 (s, 3H), 2.29 (s, 3H), 2.16 (s, 3H), 1.91-1.78 (m, 4H), 1.40 (s, 6H). MS (ESI) m/z: 406.2 [M+23]$^+$.

Example 6: Preparation of Compound 06

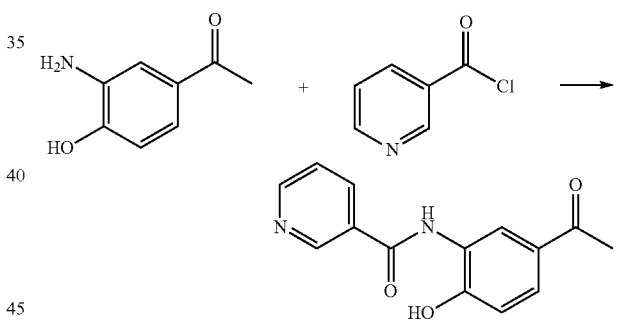

2.7 g of 1-(3-amino-4-hydroxylphenyl)ethanone was dissolved in 50 mL of pyridine, and 6.4 g of nicotinyl chloride was added under cooling in ice bath. Then, the ice bath was removed and the mixture was warmed to room temperature and stirred for 2 hours. The solvent was evaporated to dryness. 50 mL of water and 50 mL of saturated sodium carbonate aqueous solution was added. The mixture was extracted with 300 mL of dichloromethane. The organic phase was washed with 100 mL of saturated brine, and the solvent was evaporated to dryness. The residue was dissolved in 100 mL of methanol, and added with 30 mL of 4N sodium hydroxide aqueous solution. The mixture was stirred at room temperature for 1 hour, and was adjusted to pH 8-9 by adding hydrochloric acid. The solid was collected by filtration and 3.0 g of the target compound was obtained through silica-gel column chromatography. $^1$H NMR (400 MHz, DMSO-d$_6$) b 10.82 (s, 1H), 9.24 (d, J=1.5 Hz, 1H), 8.89 (dd, J=4.8, 1.6 Hz, 1H), 8.45 (dt, J=8.0, 1.9 Hz, 1H), 7.85-7.74 (m, 2H), 7.67-7.59 (m, 1H), 7.07 (d, J=8.4 Hz, 1H), 2.49 (s, 3H). MS (ESI) m/z: 257.1 [M+1]$^+$.

Example 7: Preparation of Compound 07

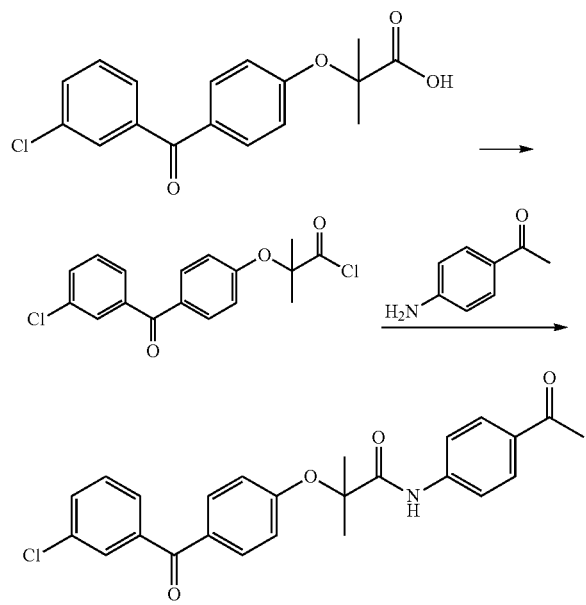

11.5 g of 2-(4-(3-chlorobenzoyl)phenoxy)-2-methylpropionic acid was dissolved in 100 mL of dichloromethane, and 6.9 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

4.05 g of p-aminoacetophenone was dissolved in 50 mL of pyridine, and the above acyl chloride in 50 mL of dichloromethane solution was added dropwise under cooling in an ice bath. After addition, the ice bath was removed; the mixture was warmed to room temperature and stirred for 2 hours. The solvent was evaporated to dryness, and the residue was dissolved by adding 200 mL of ethyl acetate, and washed successively with 200 mL of water and 100 mL of saturated brine. Then, the solvent was evaporated to dryness, and 10.5 g of the target compound was obtained through silica-gel column chromatography. $^1$H NMR (400 MHz, CDCl$_3$) δ 8.53 (s, 1H), 7.95 (s, 2H), 7.82-7.60 (m, 6H), 7.46 (d, J=6.4 Hz, 2H), 7.26 (d, J=1.5 Hz, 1H), 7.05 (d, J=6.6 Hz, 2H), 2.58 (d, J=1.4 Hz, 3H), 1.68 (s, 6H). MS (ESI) m/z: 458.3 [M+23]$^+$.

Example 8: Preparation of Compound 08

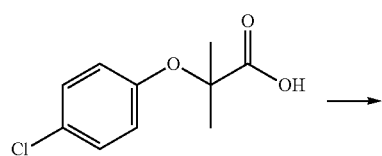

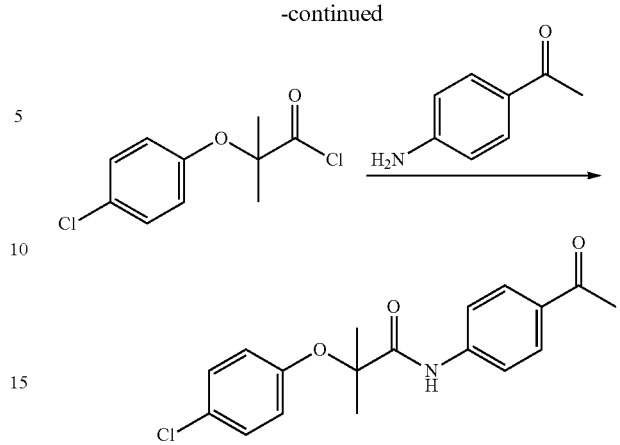

7.1 g of 2-(4-chlorophenoxy)-2-methylpropionic acid was dissolved in 100 mL of dichloromethane, and 6.3 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

4.05 g of p-aminoacetophenone was dissolved in 50 mL of pyridine, and the above acyl chloride in 50 mL of dichloromethane solution was added dropwise under cooling in an ice bath. After addition, the ice bath was removed; the mixture was warmed to room temperature and stirred for 2 hours. The solvent was evaporated to dryness, and the residue was added with 300 mL of water. The solid was collected through filtration, and then was homogenized with 50 mL of a mixed solvent of petroleum ether:ethyl acetate in 5:1. The solid was collected through filtration and dried to give 8.5 g of the target compound. $^1$H NMR (400 MHz, CDCl$_3$) δ 8.72 (s, 1H), 7.96 (d, J=8.6 Hz, 2H), 7.69 (d, J=8.6 Hz, 2H), 7.27 (d, J=9.1 Hz, 2H), 6.93 (d, J=8.7 Hz, 2H), 2.58 (s, 3H), 1.57 (s, 6H). MS (ESI) m/z: 332.3 [M+1]$^+$.

Example 9: Preparation of Compound 09

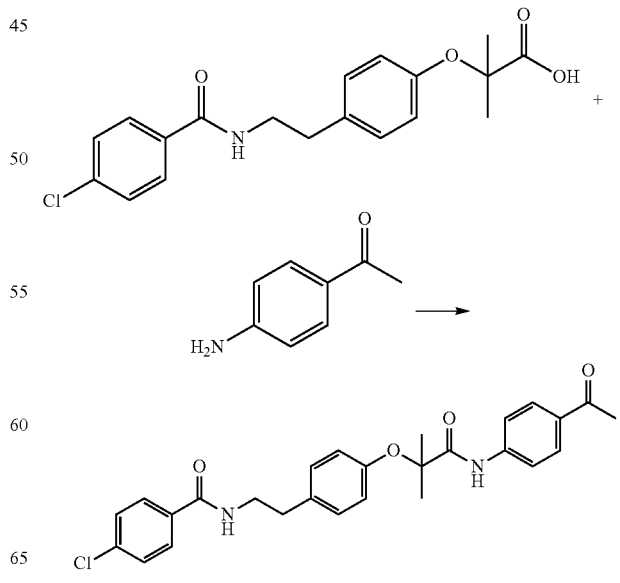

2-(4-([[3]]4-chlorobenzoyl)phenoxy)-2-methyl-propionic acid were dissolved in 50 mL of N,N-dimethylformamide, and 11.4 g of 2-(7-azobenzotriazole)-N,N,N',N'-tetramethyluronium hexafluorophosphate and 7.8 g of diisopropylethylamine were added. The resulted mixture was stirred overnight at room temperature, washed by adding 400 mL of ethyl acetate, and washed successively with 200 mL of water and 100 mL of saturated brine. Then, the solvent was evaporated to dryness, and 7.3 g of the target compound was obtained through silica-gel column chromatography. $^1$H NMR (400 MHz, CDCl$_3$) δ 8.80 (s, 1H), 7.99-7.90 (m, 2H), 7.69 (d, J=8.7 Hz, 2H), 7.65-7.58 (m, 2H), 7.40-7.31 (m, 2H), 7.16 (d, J=8.4 Hz, 2H), 6.98-6.90 (m, 2H), 6.19 (s, 1H), 3.67 (dd, J=13.1, 6.8 Hz, 2H), 2.90 (t, J=7.0 Hz, 2H), 2.58 (s, 3H), 1.57 (s, 6H). MS (ESI) m/z: 501.3 [M+23]$^+$.

Example 10: Preparation of Compound 10

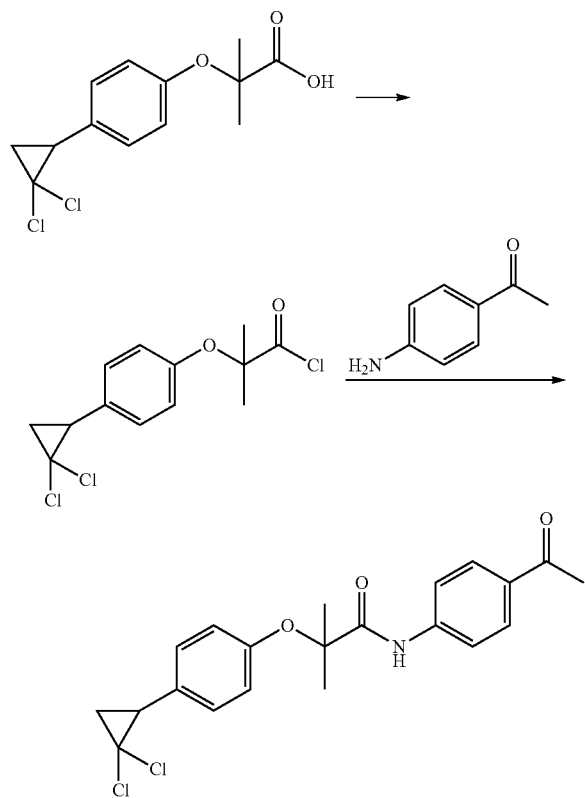

9.5 g of 2-(4-(2,2-dichlorocyclopropyl)phenoxy)-2-methylpropionic acid was dissolved in 100 mL of dichloromethane, and 6.3 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

4.05 g of p-aminoacetophenone was dissolved in 50 mL of pyridine, and the above acyl chloride in 50 mL of dichloromethane solution was added dropwise under cooling in an ice bath. After addition, the ice bath was removed; the mixture was warmed to room temperature and stirred for 2 hours. The solvent was evaporated to dryness, and the residue was dissolved by adding 200 mL of ethyl acetate, and washed successively with 200 mL of water and 100 mL of saturated brine. Then, the solvent was evaporated to dryness, and 7.2 g of the target compound was obtained through silica-gel column chromatography. $^1$H NMR (400 MHz, CDCl$_3$) δ 8.76 (s, 1H), 7.96 (d, J=8.6 Hz, 2H), 7.68 (t, J=9.5 Hz, 2H), 7.18 (t, J=9.9 Hz, 2H), 6.95 (m, 2H), 2.86 (dd, J=10.4, 8.6 Hz, 1H), 2.58 (s, 3H), 1.97 (m, 1H), 1.81 (t, J=7.9 Hz, 1H), 1.58 (s, 6H). MS (ESI) m/z: 406 [M+1]$^+$.

Example 11: Preparation of Compound 11

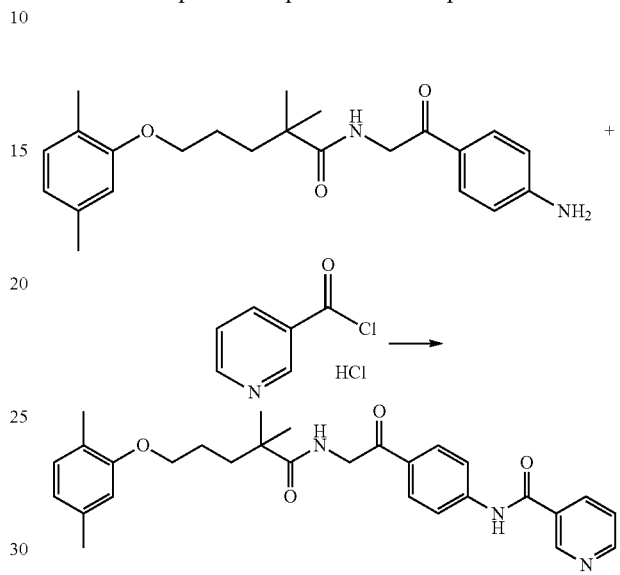

1.5 g of Compound 04 was dissolved in 20 mL of pyridine, and 0.75 g of nicotinyl chloride hydrochloride was added under cooling in an ice bath. Then the ice bath was removed, and the mixture was warmed to room temperature and stirred for 2 hours. The solvent was evaporated to dryness, and the residue was added with 100 mL of water. The solid was collected through filtration, and then was homogenized with 20 ml of a mixed solvent of petroleum ether:ethyl acetate in 3:1. The solid was collected through filtration and dried to give 1.9 g of the target compound. $^1$H NMR (400 MHz, CDCl$_3$) δ 9.22 (s, 1H), 8.95 (d, J=24.2 Hz, 1H), 8.77 (s, 1H), 8.29 (d, J=7.7 Hz, 1H), 7.97-7.89 (m, 2H), 7.89-7.82 (m, 2H), 7.46 (b, J=3.2 Hz, 1H), 6.97 (d, J=7.4 Hz, 1H), 6.80 (b, J=3.9 Hz, 1H), 6.63 (d, J=7.5 Hz, 1H), 6.59 (s, 1H), 4.66 (s, 2H), 4.01-3.75 (m, 2H), 2.28 (s, 3H), 2.15 (s, 3H), 1.82-1.68 (m, 4H), 1.27 (s, 6H). MS (ESI) m/z: 488.4 [M+1]$^+$.

Example 12: Preparation of Compound 12

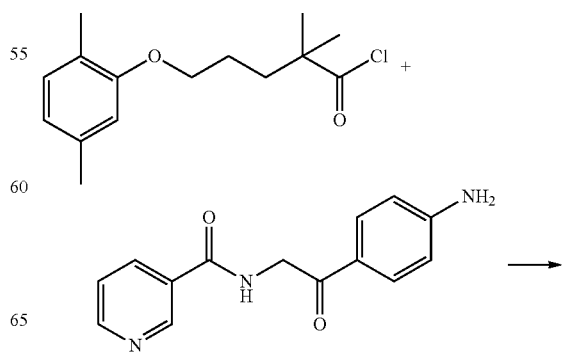

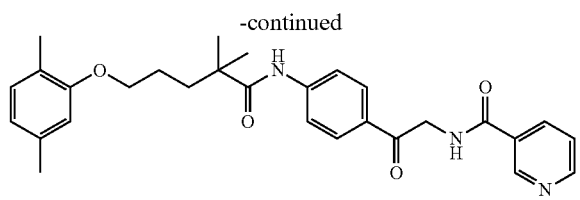

1.8 g of 5-(2,5-dimethylphenoxy)-2,2-dimethylpentanoic acid was dissolved in 30 mL of dichloromethane, and 1.4 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

1.7 g of compound JSI000844 was dissolved in 30 mL of pyridine, and the above acyl chloride in 10 mL of dichloromethane solution was added dropwise under cooling in an ice bath. After addition, the ice bath was removed; the mixture was stirred at room temperature for 3 hours. The solvent was concentrated and evaporated to dryness, and the residue was diluted by adding 100 mL of ethyl acetate, and washed successively with 50 mL of water and 50 mL of saturated brine. The solvent was evaporated to dryness, and 1.2 g of the intermediate was obtained through silica-gel column chromatography. $^1$H NMR (400 MHz, CDCl$_3$) δ 9.13 (s, 1H), 8.77 (d, J=4.2 Hz, 1H), 8.20 (d, J=7.8 Hz, 1H), 7.99 (d, J=8.6 Hz, 2H), 7.69 (d, J=8.6 Hz, 2H), 7.61 (s, 1H), 7.43 (dd, J=7.7, 4.8 Hz, 1H), 7.39-7.32 (m, 1H), 6.99 (d, J=7.5 Hz, 1H), 6.66 (d, J=7.5 Hz, 1H), 6.60 (s, 1H), 4.92 (d, J=3.9 Hz, 2H), 3.95 (s, 2H), 2.28 (s, 3H), 2.16 (s, 3H), 1.89-1.77 (m, 4H), 1.36 (s, 6H). MS (ESI) m/z: 488.9 [M+1]$^+$.

Example 13: Preparation of Compound 13

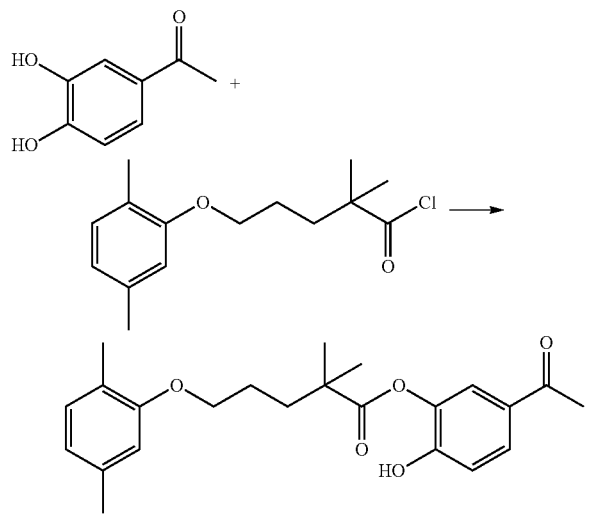

0.91 g of 1-(3,4-dihydroxyphenyl)ethanone and 0.91 g of triethylamine were dissolved in 50 mL of dichloromethane, and 1.8 g of 5-(2,5-dimethylphenoxy)-2,2-dimethylpentanoyl chloride was added under cooling in an ice bath. Then, the ice bath was removed and the mixture was warmed to room temperature and stirred for 30 min. The reaction mixture was diluted with 50 mL of dichloromethane, washed successively with 50 mL of water and 50 mL of saturated brine. The solvent was evaporated to dryness, and 2.1 g of the target compound was obtained through silica-gel column chromatography. $^1$H NMR (400 MHz, DMSO-d$_6$) δ 10.71 (s, 1H), 7.73 (dd, J=8.5, 2.1 Hz, 1H), 7.52 (d, J=2.0 Hz, 1H), 6.97 (dd, J=11.1, 8.0 Hz, 2H), 6.71 (s, 1H), 6.60 (d, J=7.4 Hz, 1H), 3.94 (s, 2H), 3.33 (s, 3H), 2.22 (s, 3H), 2.05 (s, 3H), 1.81 (m, 4H), 1.28 (s, 6H). MS (ESI) m/z: 407.2 [M+1]+.

Example 14: Preparation of Compound 14

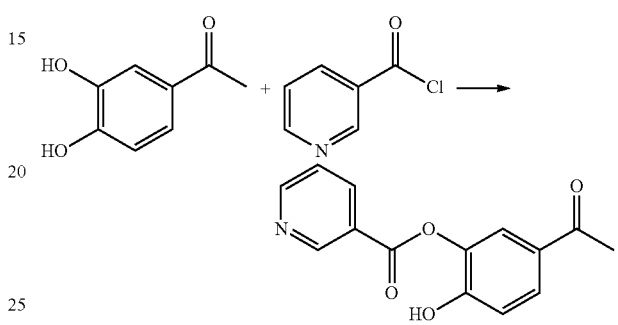

0.46 g of 1-(3,4-dihydroxyphenyl)ethanone and 0.40 g of triethylamine were dissolved in 25 mL of dichloromethane, and 0.54 g of nicotinyl chloride was added under cooling in an ice bath. Then, the ice bath was removed, and the mixture was warmed to room temperature and stirred for 1 hour. The reaction mixture was diluted with 50 mL of dichloromethane, and washed successively with 20 mL of water and 20 mL of saturated brine, followed by evaporating the solvent to dryness. The residue was added with 10 mL of saturated sodium carbonate aqueous solution and stirred, and then extracted twice with 30 mL of ethyl acetate. After the aqueous phase was separated, the mixture was adjusted to pH 7-8 with 1N hydrochloric acid, and was extracted three times with 30 mL of a mixed solution of dichloromethane and methanol (dichloromethane:methanol=10:1). The organic phases were combined and washed with 30 mL of saturated brine. The solvent was evaporated to give 0.14 g of the target compound. $^1$H NMR (400 MHz, DMSO-d$_6$) δ 10.81 (s, 1H), 9.24 (d, J=1.6 Hz, 1H), 8.89 (dd, J=4.8, 1.6 Hz, 1H), 8.45 (dt, J=8.0, 1.9 Hz, 1H), 7.86-7.75 (m, 2H), 7.64 (dd, J=7.9, 4.9 Hz, 1H), 7.05 (t, J=9.9 Hz, 1H), 2.48 (s, 3H). MS (ESI) m/z: 258.2 [M+1]$^+$.

Example 15: Preparation of Compound 15

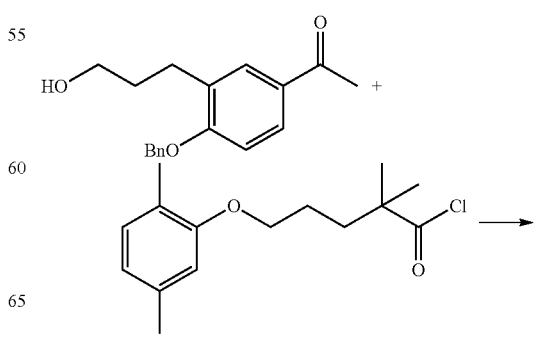

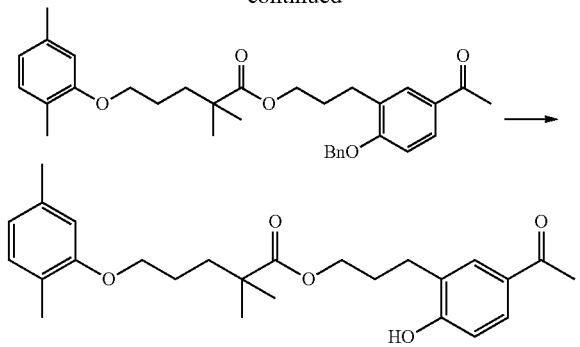

1.93 g of 5-(2,5-dimethylphenoxy)-2,2-dimethylpentanoic acid was dissolved in 20 mL of dichloromethane, and 1.5 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

2.0 g of 1-(4-phenoxy-3-(3-hydroxy)propyl)phenylethanone and 2.1 g of triethylamine were dissolved in 20 mL of dichloromethane, and the above 5-(2,5-dimethylphenoxy)-2,2-dimethylpentanoyl chloride in 10 mL of dichloromethane was added under cooling in an ice bath. Then, the ice bath was removed and the mixture was warmed to room temperature and stirred overnight. The solvent was evaporated to dryness and 1.9 g of an benzyl-protected intermediate of the target compound was obtained through silica-gel column chromatography.

The above benzyl-protected intermediate in 1.9 g and 2.3 g of ammonium formate were dissolved in 20 mL of methanol, and 0.2 g of a 5% palladium carbon hydrogenation catalyst was added, followed by stirring overnight at room temperature. The solid catalyst was removed by filtration, and the solvent of the filtrate was evaporated to dryness. Then, the residue was dissolved by adding 100 mL of ethyl acetate, and washed successively with 30 mL of water and 30 mL of saturated brine. The solvent was evaporated to dryness, and 1.5 g of the target compound was obtained through silica-gel column chromatography. $^1$H NMR (400 MHz, CDCl$_3$) δ 7.77 (d, J=2.1 Hz, 1H), 7.72 (dd, J=8.4, 2.2 Hz, 1H), 6.99 (d, J=7.5 Hz, 1H), 6.79 (d, J=8.4 Hz, 1H), 6.65 (d, J=7.5 Hz, 1H), 6.61 (s, 1H), 4.12 (t, J=6.3 Hz, 2H), 3.93 (t, J=4.9 Hz, 2H), 2.79-2.71 (m, 2H), 2.53 (s, 3H), 2.29 (s, 3H), 2.16 (s, 3H), 2.03-1.93 (m, 2H), 1.76-1.72 (m, 4H), 1.24 (s, 6H). MS (ESI) m/z: 427.3 [M+1]$^+$.

Example 16: Preparation of Compound 16

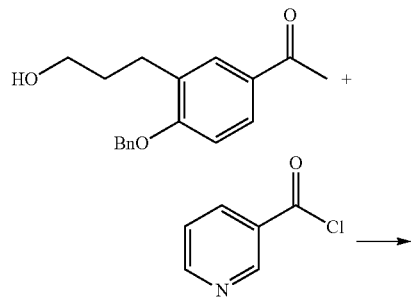

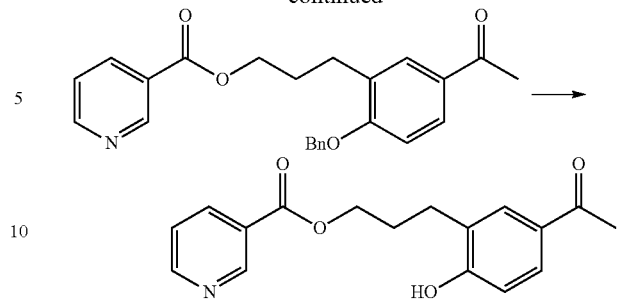

2.8 g of 1-(4-phenoxy-3-(3-hydroxyl)propyl)phenylethanone and 3.0 g of triethylamine were dissolved in 50 mL of dichloromethane, and 2.3 g of nicotinyl chloride hydrochloride was added under cooling in an ice bath. Then, the ice bath was removed, and the mixture was warmed to room temperature and stirred for 4 hours. The reaction mixture was diluted by adding 100 mL of dichloromethane, and washed successively with 50 mL of saturated aqueous sodium carbonate, 50 mL of water and 50 mL of saturated brine. The solvent was evaporated to dryness, and 2.4 g of a benzyl-protected intermediate of the target compound was obtained through silica-gel column chromatography.

The resulted benzyl-protected intermediate in 2.4 g and 3.9 g of ammonium formate were dissolved in 40 mL of methanol, and 0.3 g of a 5% palladium carbon hydrogenation catalyst was added, followed by stirring overnight at room temperature. The solid catalyst was removed by filtration, and the filtrate was evaporated to dryness. Then, the residue was dissolved by adding 100 mL of ethyl acetate, and washed successively with 30 mL of water and 30 mL of saturated brine. The solvent was evaporated to dryness, and 1.5 g of the target compound was obtained through silica-gel column chromatography. $^1$H NMR (400 MHz, CDCl$_3$) δ 9.15 (s, 1H), 8.78-8.68 (m, 1H), 8.33 (dt, J=8.0, 1.8 Hz, 1H), 7.81 (d, J=1.9 Hz, 1H), 7.69 (dd, J=8.4, 2.2 Hz, 1H), 7.44 (dd, J=7.9, 5.0 Hz, 1H), 6.84 (d, J=8.4 Hz, 1H), 4.44 (t, J=6.2 Hz, 2H), 2.87 (t, J=7.4 Hz, 2H), 2.58-2.47 (m, 3H), 2.22-2.10 (m, 2H). MS (ESI) m/z: 300.3 [M+1]$^+$.

Example 17: Preparation of Compound 17

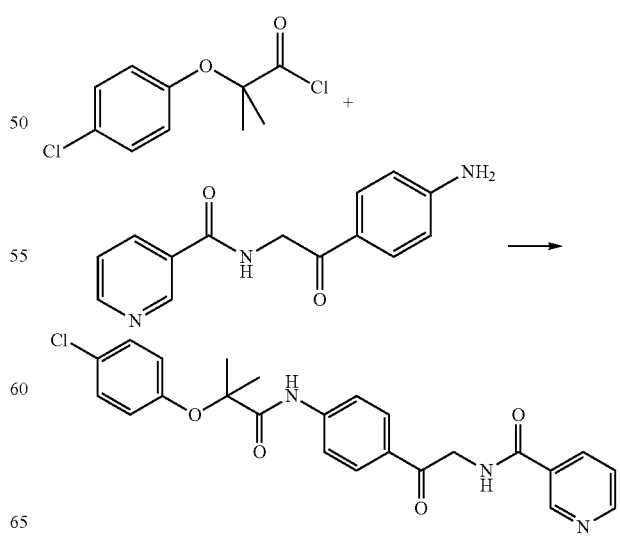

2.8 g of 2-(4-chlorophenoxyl)-2-methylpropanoic acid was dissolved in 30 mL of dichloromethane, and 2.5 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

3.0 g of compound JSI000844 was dissolved in 30 mL of pyridine, and the above acyl chloride in 10 mL of dichloromethane solution was added dropwise under cooling in an ice bath. After addition, the ice bath was removed; the mixture was stirred at room temperature for 3 hours. The solvent was concentrated and evaporated to dryness, and the residue was added with 300 mL of ice water and extracted three times with 200 mL of ethyl acetate. The organic phases were combined and washed successively with 200 mL of water and 200 mL of saturated brine. The solvent was evaporated to dryness, and 2.4 g of intermediate was obtained through silica-gel column chromatography. $^1$H NMR (400 MHz, CDCl$_3$) δ 9.13 (d, J=1.6 Hz, 1H), 8.81 (s, 1H), 8.77 (dd, J=4.8, 1.3 Hz, 1H), 8.24-8.19 (m, 1H), 8.04 (d, J=8.7 Hz, 2H), 7.78 (d, J=8.7 Hz, 2H), 7.44 (dd, J=7.9, 4.9 Hz, 1H), 7.41-7.37 (m, 1H), 7.31-7.25 (m, 3H), 6.99-6.88 (m, 2H), 4.94 (d, J=4.1 Hz, 2H), 1.58 (s, 6H). MS (ESI) m/z: 452.0 [M+1]$^+$.

Example 18: Preparation of Compound 18

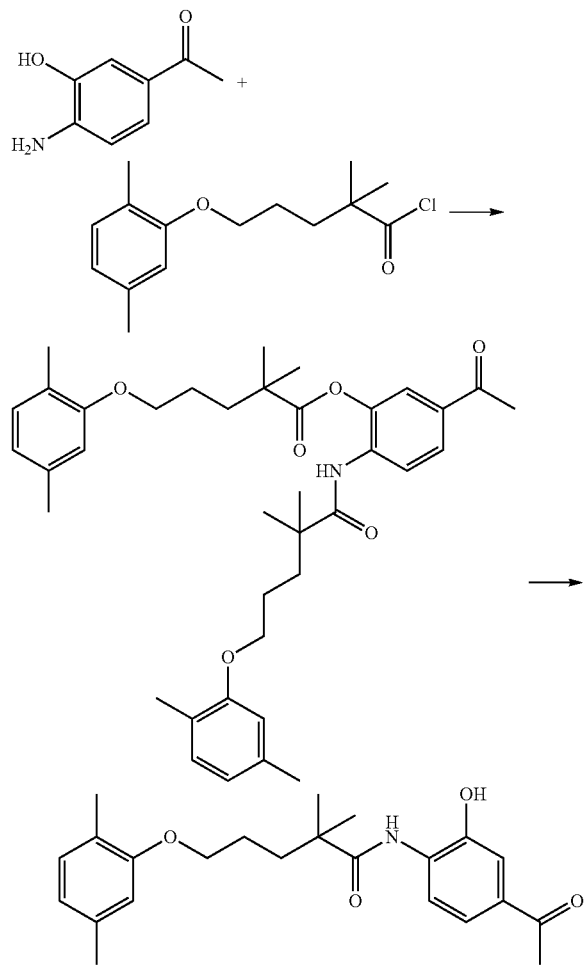

11.3 g of 5-(2,5-dimethylphenoxy)-2,2-dimethylpentanoic acid was dissolved in 100 mL of dichloromethane, and 8.6 g of oxalyl chloride and 5 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

4.5 g of 1-(4-amino-3-hydroxyphenyl)ethanone was dissolved in 50 mL of pyridine, and the resulted acyl chloride in 30 mL of dichloromethane was added dropwise under cooling in an ice bath. After addition, the ice bath was removed and the mixture was warmed to room temperature and stirred for 2 hours. The solvent was concentrated and evaporated to dryness, and the residue was added with 200 mL of ice water and extracted three times with 200 mL of ethyl acetate. The organic phases were combined and washed successively with 200 mL of 1N hydrochloric acid, 200 mL of water and 200 mL of saturated brine. The solvent was evaporated to dryness to give a diacylated intermediate.

The above intermediate was dissolved in 50 mL of methanol, and added with 15 mL of 4N aqueous sodium hydroxide solution. The resulted mixture was stirred at room temperature for 30 min, followed by pressure distillation to remove methanol. Then, the mixture was diluted by adding 50 mL of water, adjusted to pH 4-5 with 3N hydrochloric acid, and extracted with 300 mL of ethyl acetate. The organic phase was washed successively with 100 mL of water and 100 mL of saturated brine. The solvent was evaporated to dryness, and 8.3 g of the target compound was obtained through silica-gel column chromatography. $^1$H NMR (400 MHz, DMSO-d$_6$) δ 10.44 (s, 1H), 8.58 (s, 1H), 8.07 (d, J=8.4 Hz, 1H), 7.48 (dd, J=8.4, 1.9 Hz, 1H), 7.43 (d, J=1.9 Hz, 1H), 6.97 (d, J=7.5 Hz, 1H), 6.68 (s, 1H), 6.61 (d, J=7.4 Hz, 1H), 3.91 (t, J=5.8 Hz, 2H), 2.50 (s, 3H), 2.22 (s, 3H), 2.07 (s, 3H), 1.82-1.63 (m, 4H), 1.27 (s, 6H). MS (ESI) m/z: 406.0 [M+23]$^+$.

Example 19: Preparation of Compound 19

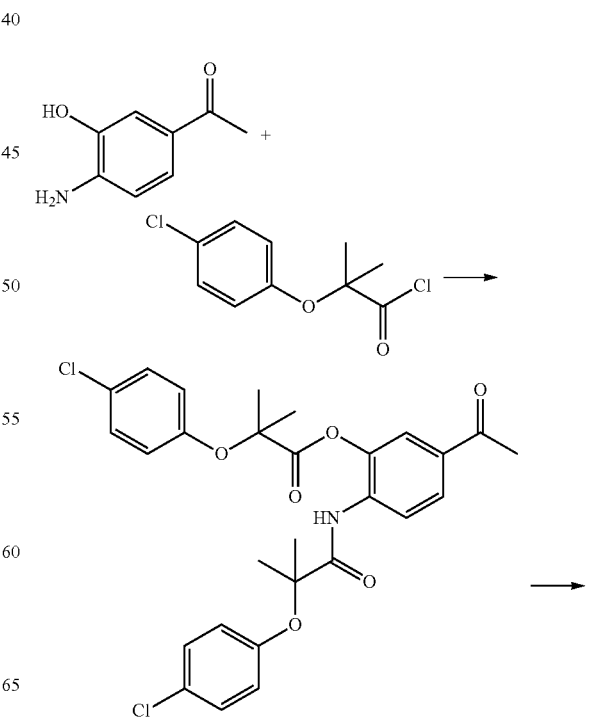

-continued

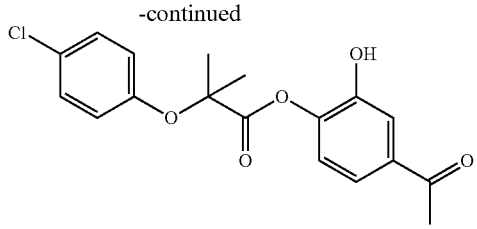

9.7 g of 2-(4-chlorophenoxy)-2-methylpropanoic acid was dissolved in 100 mL of dichloromethane, and 8.6 g of oxalyl chloride and 5 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

4.5 g of 1-(4-amino-3-hydroxyphenyl)ethanone was dissolved in 50 mL of pyridine, and the above resulted acyl chloride in 30 mL of dichloromethane was added dropwise under cooling in an ice bath. Then, the ice bath was removed and the mixture was warmed to room temperature and stirred for 2 hours. The solvent was concentrated and evaporated to dryness, and the residue was added with 200 mL of ice water and extracted three times with 200 mL of ethyl acetate. The organic phases were combined and washed successively with 200 mL of 1N hydrochloric acid, 200 mL of water and 200 mL of saturated brine. The solvent was evaporated to dryness to give a diacylated intermediate.

The above intermediate was dissolved in 50 mL of methanol, and added with 15 mL of 4N aqueous sodium hydroxide solution. The resulted mixture was stirred at room temperature for 30 min, followed by pressure distillation to remove methanol. Then, the mixture was diluted by adding 50 mL of water, adjusted to pH 4-5 with 3N hydrochloric acid, and extracted with 300 mL of ethyl acetate. The organic phase was washed successively with 100 mL of water and 100 mL of saturated brine. The solvent was evaporated to dryness, and the residual solid was homogenized with 50 mL of methanol. The solid was collected by filtration and dried to give 8.2 g of the target compound. $^1$H NMR (400 MHz, DMSO-d$_6$) δ 10.61 (s, 1H), 9.35 (s, 1H), 8.27 (d, J=8.4 Hz, 1H), 7.53 (dd, J=8.4, 1.9 Hz, 1H), 7.43 (d, J=1.9 Hz, 1H), 7.39 (d, J=8.9 Hz, 2H), 7.06 (d, J=8.9 Hz, 2H), 1.52 (s, 6H). MS (ESI) m/z: 348.0 [M+1]$^+$.

Example 20: Preparation of Compound 20

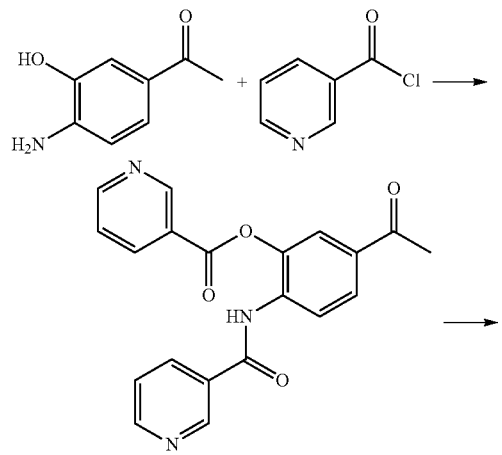

-continued

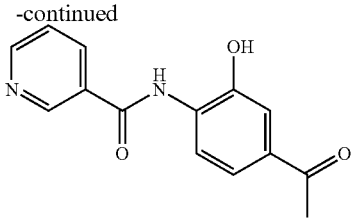

2.8 g of 1-(4-amino-3-hydroxyphenyl)ethanone was dissolved in 50 mL of pyridine, and 4.9 g of nicotinyl chloride hydrochloride was added under cooling in an ice bath. Then, the ice bath was removed and the reaction mixture was warmed to room temperature and stirred for 2 hours. The solvent was concentrated and evaporated to dryness, and the residue was added with 100 mL of ice water. The solid was collected by filtration and dried to give a diacylated intermediate.

The above intermediate was dissolved in 50 mL of methanol, and added with 10 mL of 4N aqueous sodium hydroxide solution. The resulted mixture was stirred at room temperature for 2 hours, followed by pressure distillation to remove methanol. Then, the mixture was diluted by adding 50 mL of water, adjusted to pH 3-4 with 3N hydrochloric acid, and adjusted back to pH 7-8 with saturated sodium bicarbonate solution. The solid was collected by filtration and dried to give 3.7 g of the target compound. $^1$H NMR (400 MHz, DMSO-d$_6$) δ 10.30 (s, 1H), 9.84 (s, 1H), 9.12 (d, J=1.8 Hz, 1H), 8.77 (dd, J=4.8, 1.5 Hz, 1H), 8.36-8.20 (m, 1H), 7.98 (d, J=8.3 Hz, 1H), 7.60-7.55 (m, 1H), 7.52 (dd, J=8.3, 1.9 Hz, 1H), 7.48 (d, J=1.9 Hz, 1H), 2.54 (s, 3H). MS (ESI) m/z: 257.0 [M+1]$^+$.

Example 21: Preparation of Compound 21

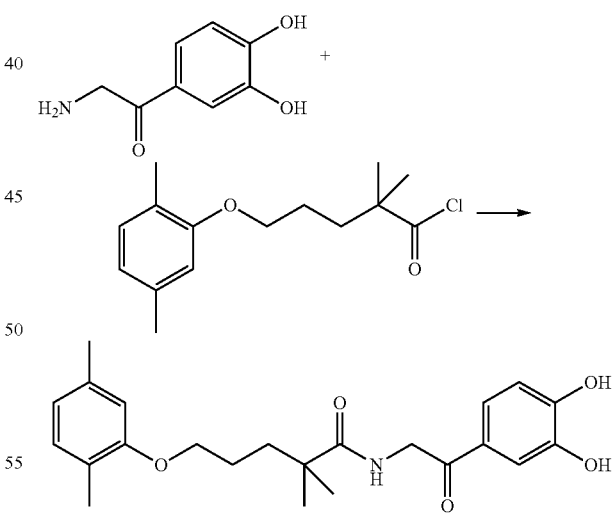

15 g of 5-(2,5-dimethylphenoxy)-2,2-dimethylpentanoic acid was dissolved in 150 mL of dichloromethane, and 11.4 g of oxalyl chloride and 2 drops of N,N-dimethylformamide were added under cooling in an ice bath. Then, the ice bath was removed and the mixture was warmed to room temperature and stirred for 3 hours. The solvent was evaporated to dryness to give corresponding acyl chloride.

10 g of 2-amino-1-(3,4-dihydroxyphenyl)ethyl ketone was dissolved in 100 mL of pyridine, and the above acyl chloride in 50 mL of dichloromethane solution was added dropwise under cooling in an ice bath. After the addition, the ice bath was removed and the mixture was stirred at room temperature for 2 hours. The solvent was concentrated and evaporated to dryness, and the residue was diluted by adding 300 mL of ethyl acetate, and washed successively with 100 mL of 3N hydrochloric acid, 100 mL of water and 100 mL of saturated brine. The solvent was evaporated to dryness, and 7.2 g of the target compound was obtained through silica-gel column chromatography. $^1$H NMR (400 MHz, CD$_3$OD) δ 7.46-7.37 (m, 2H), 6.92 (d, J=7.4 Hz, 1H), 6.83 (d, J=8.1 Hz, 1H), 6.65 (s, 1H), 6.59 (d, J=7.3 Hz, 1H), 4.55 (s, 2H), 3.92 (t, J=5.6 Hz, 2H), 2.25 (s, 3H), 2.12 (s, 3H), 1.82-1.67 (m, 4H), 1.26 (s, 6H). MS (ESI) m/z: 422.0 [M+23]$^+$.

Example 22: Preparation of Compound 22

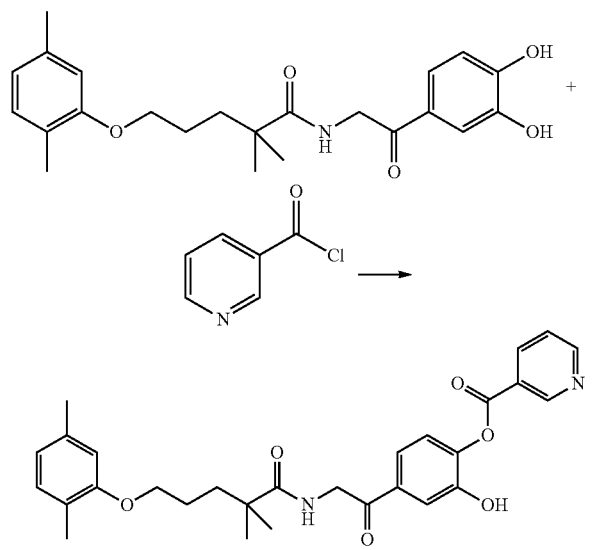

5.4 g of Compound 21 and 2.7 g of triethylamine were dissolved in 200 mL of dichloromethane, and 2.9 g of nicotinyl chloride was added under cooling in an ice bath. Then, the ice bath was removed and the mixture was stirred overnight at room temperature. The reaction mixture was diluted by adding 100 mL of dichloromethane, and washed successively with 100 mL of water and 100 mL of saturated brine. The solvent was evaporated to dryness, and 3.5 g of the target compound was obtained through silica-gel column chromatography. $^1$H NMR (400 MHz, CDCl$_3$) δ 9.34 (d, J=1.2 Hz, 1H), 8.78-8.72 (m, 1H), 8.39-8.33 (m, 1H), 7.78 (d, J=2.0 Hz, 1H), 7.64 (dd, J=8.6, 2.0 Hz, 1H), 7.41 (dd, J=7.7, 5.0 Hz, 1H), 7.11 (d, J=8.5 Hz, 1H), 6.96 (d, J=7.5 Hz, 1H), 6.89 (s, 1H), 6.62 (d, J=7.6 Hz, 1H), 6.58 (s, 1H), 4.60 (d, J=4.1 Hz, 3H), 3.89 (s, 3H), 2.27 (s, 3H), 2.14 (s, 3H), 1.74 (s, 4H), 1.27 (s, 6H). MS (ESI) m/z: 505.0 [M+1]+.

Pharmacological and Biological Activity Tests

1. Therapeutic Effect on Fatty Liver Diseases of SD Rats

Preparation Process of Lipid Emulsion:

500 g of lard oil was taken, placed in a container, and heated to melt. When the temperature rose to 100° C., it was added with 200 g of cholesterol to dissolve completely, and then further added with 20 g of propylthiouracil. The resulted mixture was stirred well, and added with 500 ml of Tween 80 after dissolution, resulting in an oil phase. At the same time, 600 mL of distilled water and 400 mL of 1,2-propanediol were taken and heated to 60° C. in a water bath, then were added with 40 g of sodium deoxycholate. The resulted mixture was stirred well until realizing complete dissolution, so as to give an aqueous phase. The aqueous phase was added into the oil phase and mixed well to give a lipid emulsion. The lipid emulsion was heated in a water bath of 37° C. before intragastric administration to animals.

Pharmaceuticals:

An appropriate amount of pharmaceutical was weighed, added with 0.5% CMC-Na, and mixed homogeneously by grinding. There are groups for Compound 01 (80 mg/kg), Compound 02 (80 mg/kg), Compound 03 (80 mg/kg), Compound 04 (80 mg/kg), Compound 05 (80 mg/kg), Compound 06 (80 mg)/kg), Compound 07 (80 mg/kg), Compound 08 (80 mg/kg), Compound 09 (80 mg/kg), Compound 10 (80 mg/kg), Compound 11 (80 mg/kg), Compound 12 (80 mg/kg), Compound 13 (80 mg/kg), Compound 14 (80 mg/kg), Compound 15 (80 mg/kg), Compound 16 (80 mg/kg), Compound 17 (80 mg/kg), Compound 18 (80 mg/kg), Compound 19 (80 mg/kg), Compound 20 (80 mg/kg), Compound 21 (80 mg/kg), and Compound 22 (80 mg/kg).

Experimental Animals:

Male SD rats weighing 180-200 g were fed adaptively for 7 days. Based on body weight, 10 animals were used as control and the remaining animals were intragastrically administered with the lipid emulsion every day, 1 ml/100 g body weight for 14 days. After fasting for 12 hours, 1 mL of blood was collected from the orbits of the animals, and was determined by Hitachi Automatic Biochemical Analyzer 7080 for serum cholesterol (CHO), triglyceride (TG), low density lipoprotein (LDL-C) and high density lipoprotein (HDL-C).

According to TC values, the animals, which were administrated with the lipid emulsion, were divided into Model group, Simvastatin group (Sim, 10 mg/kg), Obeticholic Acid group (10 mg/kg) and Compound 01~22 groups (80 mg/kg). The modeled rats were continued with the intragastric administration of the lipid emulsion. At the same time, the pharmaceutical-administered groups were administrated with a corresponding dose of pharmaceuticals, while the Model group was administrated with an equal volume of solvent. The pharmaceutical-administered groups were administrated with the lipid emulsion in the morning, and with the pharmaceuticals in the afternoon. The animals were measured for the body weight once a week, and were observed. After 14 days of continuous administration, 1 mL of blood was collected from the orbits, and was determined for the contents of triglyceride, cholesterol, low density lipoprotein and high density lipoprotein in blood serum. It was shown by the experimental results that the blood lipid levels of the pharmaceutical-administered groups had no obvious change, and Obeticholic Acid had no blood lipid-reducing effect. The experimental results are shown in Table 1. The functions of liver and kidney were tested after 4 weeks and the results are shown in Table 2.

TABLE 1

Influence of the Compounds on the contents of triglyceride, cholesterol, low density lipoprotein and high density lipoprotein in blood serum.

| Groups | CHO | TG | HDL-C | LDL-C |
|---|---|---|---|---|
| Control | 1.65 ± 0.13 | 0.52 ± 0.17 | 1.06 ± 0.10 | 0.43 ± 0.03 |
| Model | 4.54 ± 0.27▲ | 1.01 ± 0.19 | 1.68 ± 0.09▲ | 2.78 ± 0.75▲ |
| Compound 02 80 mg/kg | 4.29 ± 0.65 | 0.51 ± 0.19 | 1.74 ± 0.29 | 2.18 ± 0.71 |
| Compound 09 80 mg/kg | 4.56 ± 1.24 | 0.71 ± 0.16 | 1.77 ± 0.41 | 2.47 ± 1.06 |
| Compound 12 80 mg/kg | 4.03 ± 0.47 | 0.33 ± 0.05* | 1.92 ± 0.11* | 2.16 ± 0.05 |
| Compound 21 80 mg/kg | 4.37 ± 0.62 | 0.80 ± 0.13 | 1.99 ± 0.44 | 2.09 ± 0.68 |
| Compound 22 80 mg/kg | 4.36 ± 1.08 | 0.57 ± 0.27 | 1.47 ± 0.51 | 2.87 ± 1.25 |
| Obeticholic Acid 10 mg/kg | 4.74 ± 0.34 | 0.52 ± 0.06 | 1.68 ± 0.22 | 2.85 ± 1.00* |

Note:
▲$p < 0.05$,
▲▲$p < 0.01$ vs Control;
*$p < 0.05$,
**$p < 0.01$ vs Model.

TABLE 2

Liver functions of rats after administration for 4 weeks

| Groups | AST | ALT | ALP | TBIL |
|---|---|---|---|---|
| Control | 134.67 ± 50.56 | 48.67 ± 2.08 | 896.00 ± 75.48 | 1.33 ± 0.35 |
| Model | 263.67 ± 137.59▲ | 152.00 ± 137.07▲ | 1170.33 ± 227.29▲ | 4.67 ± 0.21▲▲ |
| Compound 02 80 mg/kg | 187.00 ± 36.44* | 62.52 ± 13.24* | 1001.52 ± 273.34 | 1.98 ± 0.81** |
| Compound 09 80 mg/kg | 172.08 ± 21.93* | 77.52 ± 8.13* | 996.33 ± 275.12 | 2.73 ± 1.11* |
| Compound 12 80 mg/kg | 137.75 ± 31.74* | 54.00 ± 5.72** | 994.50 ± 150.68* | 3.25 ± 2.11 |
| Compound 21 80 mg/kg | 184.40 ± 18.68 | 65.6 ± 27.20* | 1074.00 ± 181.32 | 3.23 ± 1.35 |
| Compound 22 80 mg/kg | 180.60 ± 27.19 | 58.00 ± 2.55* | 874.33 ± 251.66 | 2.97 ± 1.53* |
| Obeticholic Acid 10 mg/kg | 248.20 ± 156.61 | 136.40 ± 62.68 | 999.60 ± 354.29 | 4.06 ± 1.40 |

Note:
▲$p < 0.05$,
▲▲$p < 0.01$ vs Control;
*$p < 0.05$,
**$p < 0.01$ vs Model.

Experimental Results:

The results of pathological sections after pharmaceutical treatment of fatty liver of the SD rats are shown in Table 3. In Table 3, the pathological results were scored, and the lesion degrees were expressed as follows: "0-±": 0-25% of hepatocytes undergoing steatosis; "+": 25-45% of hepatocytes undergoing steatosis; "++": 45-65% of hepatocytes undergoing steatosis; "+++": 65-85% or more of hepatocytes undergoing steatosis; "++++": a large amount of macrovesicular changes; "0-±": no or suspicious infiltration of inflammatory cells; "+–++": a small amount of infiltration of inflammatory cells; "++–+++": moderate infiltration of inflammatory cells; "++++": severe infiltration of inflammatory cells.

TABLE 3

Therapeutic effect of tested compounds on fatty liver of rats and pathological grading

| | Pathological grading | | | | | | | | | |
|---|---|---|---|---|---|---|---|---|---|---|
| | Steatotic hepatocytes | | | | | Infiltration of inflammatory cells | | | | |
| Groups | 1 | 2 | 3 | 4 | 5 | 1 | 2 | 3 | 4 | 5 |
| Control | ± | 0 | 0 | ± | 0 | 0 | 0 | 0 | 0 | 0 |
| Model | +++ | ++++ | +++ | ++++ | ++++ | ++ | +++ | ++ | +++ | +++ |
| Sim | ++ | ++ | +++ | ++ | ++ | ++ | ++ | ++ | ++ | ++ |
| OCA | ++ | ++ | ++ | +++ | ++ | ++ | ++ | + | ++ | ++ |
| Compound 01 | ++ | ++ | ++ | ++ | ++ | + | + | + | + | + |

TABLE 3-continued

Therapeutic effect of tested compounds on fatty liver of rats and pathological grading

| | Pathological grading | | | | | | | | | |
|---|---|---|---|---|---|---|---|---|---|---|
| | Steatotic hepatocytes | | | | | Infiltration of inflammatory cells | | | | |
| Groups | 1 | 2 | 3 | 4 | 5 | 1 | 2 | 3 | 4 | 5 |
| Compound 02 | + | + | ++ | + | ++ | + | ± | + | + | + |
| Compound 03 | ++ | + | +++ | ++ | ++ | + | + | ++ | + | + |
| Compound 04 | ++ | ++ | ++ | +++ | ++ | + | + | ++ | ++ | + |
| Compound 05 | + | +++ | ++ | ++ | + | + | ++ | ++ | + | + |
| Compound 06 | + | ++ | ++ | + | ++ | + | ++ | + | + | ++ |
| Compound 07 | ++ | ++ | ++ | ++ | + | ++ | ++ | + | + | ++ |
| Compound 08 | ++ | ++ | + | ++ | + | + | + | + | + | + |
| Compound 09 | + | + | + | + | + | 0 | + | + | 0 | + |
| Compound 10 | ++ | ++ | + | ++ | ++ | + | ++ | + | + | + |
| Compound 11 | + | ++ | ++ | ++ | + | + | + | + | + | + |
| Compound 12 | 0 | ± | 0 | 0 | ± | 0 | ± | 0 | ± | 0 |
| Compound 13 | + | ++ | + | ++ | ++ | ++ | + | + | + | + |
| Compound 14 | + | +± | + | + | +± | 0 | ± | + | + | ± |
| Compound 15 | ++ | +++ | ++ | ++ | ++ | + | ++ | + | + | ++ |
| Compound 16 | + | ++ | +++ | ++ | + | + | + | ++ | ++ | + |
| Compound 17 | + | ++ | ++ | ++ | ++ | + | + | + | + | ++ |
| Compound 18 | + | + | ++ | ++ | ++ | + | ++ | + | + | + |
| Compound 19 | ++ | ++ | ++ | +++ | + | + | + | ++ | + | + |
| Compound 20 | ++ | +++ | ++ | ++ | ++ | ++ | + | + | + | + |
| Compound 21 | + | 0 | + | + | + | + | + | + | 0 | + |
| Compound 22 | + | + | ++ | + | + | + | + | + | + | + |

Simple fatty liver has the following characteristics: more than 30% of hepatocytes in a low-power field have steatosis, but there are no other obvious histological changes, that is, no inflammation, necrosis and fibrosis. The one having, in the visual field, 30% to 50% of hepatocytes with steatosis has low-grade fatty liver; 50% to 75% of hepatocytes with steatosis would be mid-grade fatty liver; more than 75% of hepatocytes with steatosis would be severe fatty liver. The one having, in a low-power field, <30% of hepatocytes with steatosis is called fatty change of liver.

The results in Table 3 show that the compounds can significantly reduce hepatic steatosis and the infiltration of inflammatory cells. Thus, it is demonstrated that Compounds 1-22 have significant therapeutic effect on fatty liver.

2. Experiments of Weight Loss 2.1 Therapeutic Effect on Nutritive Obesity C57 Mice Animals:

C57 mice, male, 18-20 g of body weight. The mice were randomly divided into Control group, Model group, Orlistat group, Compound 13 group and Compound 14 group, with 6 mice in each group.

Pharmaceuticals:

appropriate amounts of orlistat, Compound 13 and Compound 14 were weighed respectively, added with 0.5% CMC-Na and grinded to dissolve.

Experimental Process:

The mice in Control group were fed with normal diet, and the other mice were fed with high-fat diet. All of the mice had free access to water. After one week of feeding, the pharmaceuticals were intragastrically administered. The dose was 40 mg/kg body weight for orlistat, 80 mg/kg for Compounds 13 and 14. The body weight of the mice was weighed every week during the experiment which lasted for 28 days.

The experimental results are shown in Table 4.

TABLE 4 effect of tested compounds on body weight of mice in the experiment with nutritive obesity C57 mice ($\bar{x} \pm s$, n = 6)

| Experiment Days | Control | Model | Orlistat | Compound 13 | Compound 14 |
|---|---|---|---|---|---|
| 0 | 17.83 ± 0.54 | 18.08 ± 0.64 | 18.28 ± 0.65 | 17.20 ± 1.92 | 17.21 ± 1.57 |
| 7 | 19.20 ± 0.92 | 20.44 ± 0.62 | 20.29 ± 0.63 | 19.97 ± 0.57 | 19.83 ± 0.71 |
| 14 | 20.84 ± 1.07 | 23.01 ± 0.54 | 21.39 ± 0.70 | 21.04 ± 0.29 | 20.87 ± 0.75 |
| 21 | 21.62 ± 0.82 | 25.09 ± 0.61 | 22.51 ± 0.73 | 22.14 ± 0.31 | 21.89 ± 0.77 |
| 28 | 23.73 ± 1.11 | 26.30 ± 0.71[##] | 24.47 ± 0.79** | 23.25 ± 0.26**[▲] | 22.92 ± 0.88**[▲] |

Note:
[▲]$p < 0.05$,
[▲▲] $p < 0.01$ vs Orlistat;
*$p < 0.05$,
**$p < 0.01$ vs Model,
[#] $p < 0.05$,
[##]$p < 0.01$ vs Control As shown by Table 4, Compounds 13 and 14 can significantly decrease the body weight of the mice from Day 14 as compared with Model group, and have better effect than Orlistat.

2.2 Experiment of the Weight Loss Effect of Tested Compounds on Ob/Ob Mice

Animals:

36 ob/ob mice, male, 18-20 g of body weight, fed adaptively for one week before use. The mice were randomly divided into Control group, Model group, Orlistat group, Compound 13 group and Compound 14 group, with 6 mice in each group.

Pharmaceuticals:

appropriate amounts of orlistat, Compound 13 and Compound 14 were weighed respectively, added with 0.5% CMC-Na and grinded to dissolve.

Experimental Process:

After feeding for one week, the mice were intragastrically administrated with the pharmaceuticals except the mice of Control group. The dose was 40 mg/kg body weight for orlistat, 80 mg/kg for the other pharmaceuticals. The body weight of the mice was weighed every week during the experiment which lasted for 28 days.

TABLE 5

Experiment of the weight loss effect of tested compounds on ob/ob mice ($\bar{x} \pm s$, n = 6).

| Experiment Days | Control | Orlistat | Compound 13 | Compound 14 |
|---|---|---|---|---|
| 0 | 21.02 ± 1.05 | 20.53 ± 0.50 | 20.74 ± 1.10 | 20.79 ± 0.39 |
| 7 | 27.68 ± 2.11 | 22.82 ± 1.79 | 21.43 ± 0.61 | 21.22 ± 0.38 |
| 14 | 30.95 ± 1.47 | 23.98 ± 1.85 | 22.10 ± 0.16 | 22.18 ± 0.42 |
| 21 | 35.25 ± 1.86 | 26.86 ± 1.99 | 24.53 ± 1.76 | 24.10 ± 0.45 |
| 28 | 38.64 ± 1.55 | 31.23 ± 2.31* | 26.10 ± 1.95**▲ | 26.17 ± 0.86**▲ |

Note:
▲$p < 0.05$,
▲▲ $p < 0.01$ vs Orlistat;
*$p < 0.05$,
**$p < 0.01$ vs Control As shown by Table 5, Compounds 13 and 14 can significantly decrease the body weight of the ob/ob mice as compared with Model group, and have better effect than Orlistat.

3. Acute Toxicity Test

A single oral-dose method was employed.

Animals:

ICR mice, 18-20 g of body weight, 20 mice in each group, half male and half female.

Experimental Pharmaceuticals:

Compound 01 (5 g/kg), Compound 02 (5 g/kg), Compound 08 (5 g/kg), Compound 09 (5 g/kg), Compound 12 (5 g/kg), Compound 13 (5 g/kg), compound 14 (5 g/kg), compound 18 (5 g/kg), compound 21 (5 g/kg), compound 22 (5 g/kg). The pharmaceuticals were added with 0.5% CMC-Na, ground and mixed well for reserve.

Experimental Process:

After fasting for 16 h, the animals were orally and intragastrically administrated with the tested pharmaceuticals in a single dose respectively. After administration, the mice were fasted for another 3-4 h. The general conditions of the animals were closely observed for 6 h after the administration, and further observed for 14 days.

Experimental Results:

No animal died during the experiment and no abnormal condition was observed.

Acute toxicity: ID50≥5 g/kg.

What is claimed is:

1. A compound of Formula I or a pharmaceutically acceptable salt thereof,

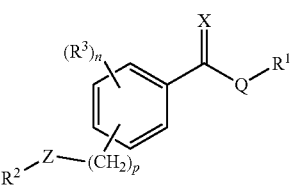

wherein,

X is selected from oxygen;

Z is selected from imino;

Q is selected from methylene (—CH$_2$—);

$R^1$ is selected from

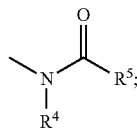

$R^2$ is selected from

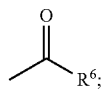

$R^3$ is selected from H; halogen; hydroxyl; amino; nitro; cyano; C1-C10 alkyl; C1-C10 alkoxyl; or C3-C10 cycloalkyl, n is an integer selected from 0 to 1;

p is 0;

wherein, $R^4$ is selected from H or C1-C10 alkyl;

$R^5$ or $R^6$ is independently selected from the optionally substituted groups of: phenyl; 5- to 6-membered monocyclic heteroaryl having 1 to 4 heteroatom(s) independently selected from nitrogen; or

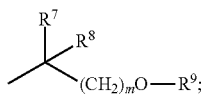

wherein $R^7$ or $R^8$ is independently selected from H or from substituted or unsubstituted C1-C10 alkyl;

$R^9$ is selected from phenyl, monosubstituted phenyl or multi-substituted phenyl, wherein the substituent for phenyl is selected from halogen; hydroxyl; C1-C10 alkyl; or C1-C10 alkoxyl, m is an integer selected from 0 to 8;

said "substituted" refers to substituents chosen from halogen; C1-C10 alkyl; C3-C10 cycloalkyl; C1-C10 alkyl substituted with C5-C10 aryl; C5-C10 aryl; 3- to 10-membered heterocyclic group having 1 to 3 heteroatom(s) independently selected from nitrogen or oxygen; or 5- to 10-membered heteroaryl having 1 to 4 heteroatom(s) independently selected from nitrogen or oxygen.

2. The compound of Formula I or a pharmaceutically acceptable salt thereof according to claim 1, wherein, $R^4$ is selected from H or from C1-C6 alkyl;

$R^7$ or $R^8$ is independently selected from H or from substituted or unsubstituted C1-C6 alkyl;

$R^9$ is selected from phenyl, monosubstituted phenyl or multi-substituted phenyl, wherein the substituent for phenyl is selected from halogen; hydroxyl; C1-C6 alkyl; or C1-C6 alkoxyl.

3. The compound of Formula I or a pharmaceutically acceptable salt thereof according to claim 1, wherein, $R^3$ is selected from H; halogen; hydroxyl; amino; nitro; cyano; C1-C3 alkyl; C1-C3 alkoxyl; or C3-C6 cycloalkyl, $R^7$ or $R^8$ is independently selected from —$CH_3$;

$R^9$ is selected from monosubstituted phenyl or disubstituted phenyl, wherein the substituent for phenyl is halogen or —$CH_3$.

4. The compound of Formula I or a pharmaceutically acceptable salt thereof according to claim 1, wherein $R^5$ and $R^6$ are pyridin-3-yl.

5. The compound of Formula I or a pharmaceutically acceptable salt thereof according to claim 1, wherein $R^7$ and $R^8$ is methyl.

6. The compound of Formula I or a pharmaceutically acceptable salt thereof according to claim 1, wherein $R^9$ is 2,5-dimethyl phenyl.

7. The compound of Formula I or a pharmaceutically acceptable salt thereof according to claim 1, wherein m is 3.

8. The compound of Formula I or a pharmaceutically acceptable salt thereof according to claim 1, wherein the halogen is chlorine; $R^4$ is H.

9. The compound of Formula I or a pharmaceutically acceptable salt thereof according to claim 1, comprising compounds having the following structures:

11

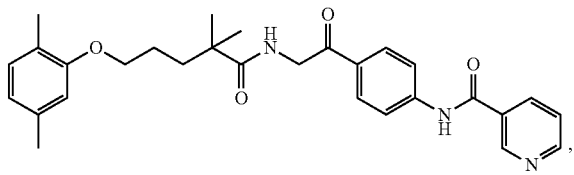

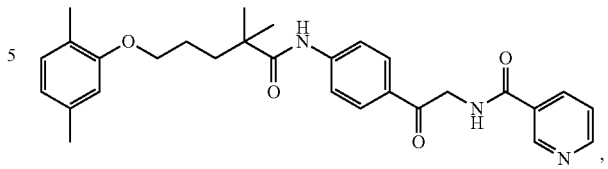

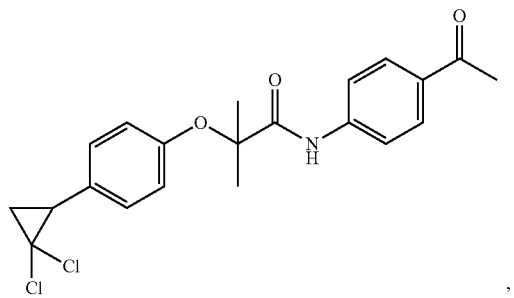

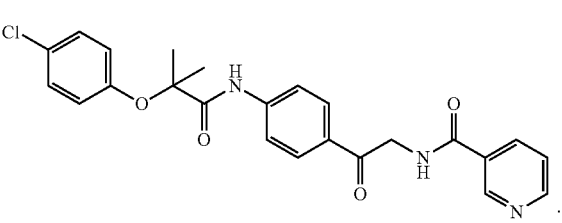

10. The compound of Formula I or a pharmaceutically acceptable salt thereof according to claim 2, wherein $R^5$ and $R^6$ are pyridin-3-yl.

11. The compound of Formula I or a pharmaceutically acceptable salt thereof according to claim 2, wherein $R^7$ and $R^8$ is methyl.

12. The compound of Formula I or a pharmaceutically acceptable salt thereof according to claim 2, wherein $R^9$ is 2,5-dimethyl phenyl.

13. The compound of Formula I or a pharmaceutically acceptable salt thereof according to claim 3, wherein $R^5$ and $R^6$ are pyridin-3-yl.

14. The compound of Formula I or a pharmaceutically acceptable salt thereof according to claim 3, wherein $R^7$ and $R^8$ is methyl.

15. The compound of Formula I or a pharmaceutically acceptable salt thereof according to claim 3, wherein $R^9$ is 2,5-dimethyl phenyl.

16. A method for preparing the compounds of Formula I or a pharmaceutically acceptable salt thereof as defined in claim 1, wherein the compounds of Formula I in which $R^2$ is

are represented by Formula I-A and the reaction is as follows:

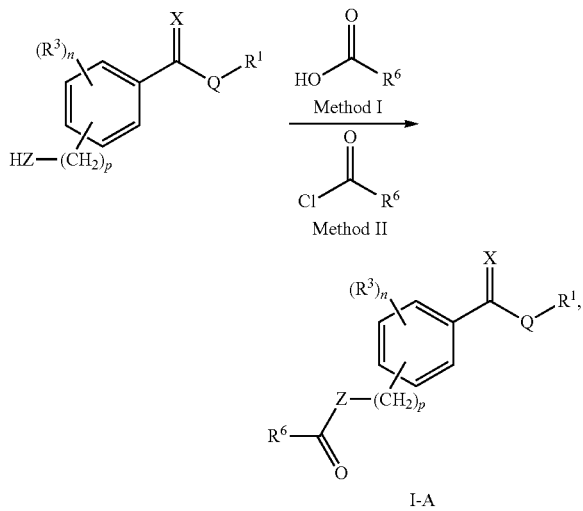

the method comprising:

Method I, comprising a step of directly condensing an acid

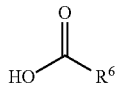

and a compound

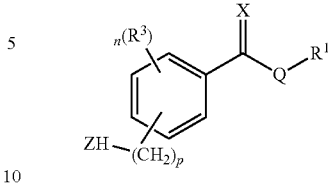

in the presence of a condensing agent and a solvent; or
Method II, comprising a step of condensing an acyl chloride and a compound

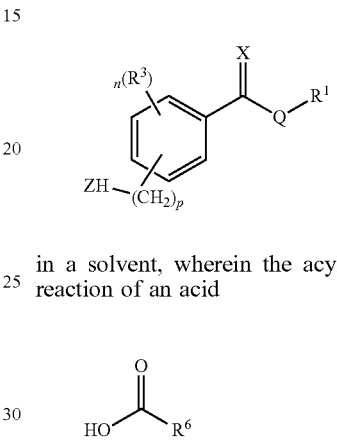

in a solvent, wherein the acyl chloride is obtained by a reaction of an acid

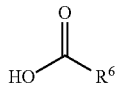

with a chlorinating agent.

17. A pharmaceutical composition comprising the compound of Formula I or a pharmaceutically acceptable salt thereof as defined in claim 1, and a pharmaceutically acceptable additive.

18. The pharmaceutical composition according to claim 17, wherein the pharmaceutical composition is in a form of tablet, pill, powder, liquid, suspension, emulsion, granule, capsule, suppository or injection.

* * * * *